United States Patent
Hoey et al.

(10) Patent No.: US 11,284,931 B2
(45) Date of Patent: Mar. 29, 2022

(54) MEDICAL SYSTEMS AND METHODS FOR ABLATING AND ABSORBING TISSUE

(75) Inventors: Michael Hoey, Shoreview, MN (US); John H. Shadduck, Berkeley, CA (US)

(73) Assignee: Tsunami MedTech, LLC, Menlo Park, CA (US)

(*) Notice: Subject to any disclaimer, the term of this patent is extended or adjusted under 35 U.S.C. 154(b) by 102 days.

(21) Appl. No.: 12/699,795

(22) Filed: Feb. 3, 2010

(65) Prior Publication Data

US 2010/0262133 A1    Oct. 14, 2010

Related U.S. Application Data

(60) Provisional application No. 61/206,823, filed on Feb. 3, 2009.

(51) Int. Cl.
| | | |
|---|---|---|
| *A61B 18/04* | (2006.01) | |
| *A61B 18/06* | (2006.01) | |

(52) U.S. Cl.
CPC ............ *A61B 18/04* (2013.01); *A61B 18/06* (2013.01); *A61B 2018/048* (2013.01)

(58) Field of Classification Search
CPC ..... A61B 18/04; A61B 18/042; A61B 18/048; A61B 18/28; A61B 2018/00577; A61B 2018/00595; A61B 2018/00589; A61B 2018/00625; A61B 2018/00636; A61B 2018/00696; A61B 2018/00702; A61B 2018/00714; A61B 2018/048; A61B 2018/00791; A61B 2018/00642; A61B 2018/00011; A61B 2018/00017; A61B 2018/00744; A61B 17/3203; A61B 2017/00084; A61B 2017/008; A61B 18/06; A61B 18/08; A61B 18/10; A61B 18/12;

(Continued)

(56) References Cited

U.S. PATENT DOCUMENTS

| | | |
|---|---|---|
| 408,899 A | 8/1889 | Bioch et al. |
| 697,181 A | 4/1902 | Smith |

(Continued)

FOREIGN PATENT DOCUMENTS

| | | |
|---|---|---|
| WO | WO 2000/011927 | 3/2000 |
| WO | WO 2000/029055 | 5/2000 |

(Continued)

OTHER PUBLICATIONS

Coda, et al., "Effects of pulmonary reventilation on gas exchange after cryolytic disobstruction of endobronchial tumors," *Minerva Medical*, vol. 72, pp. 1627-1631, Jun. 1981 (with English translation).

(Continued)

*Primary Examiner* — Khadijeh A Vahdat
(74) *Attorney, Agent, or Firm* — Levine Bagade Han LLP

(57) ABSTRACT

Methods, devices, and systems are described herein for applying energy to tissue for ablation of tissue while allowing the tissue to be resorbed within the body. Such methods, devices, and systems control application of energy to maintain a temperature of target tissue above an ablation temperature, being dependent upon the activation time, and below a transformation temperature, also being dependent upon the activation time, where the transformation prevents or hinders resorption of the treated tissue by the body.

23 Claims, 25 Drawing Sheets

(58) Field of Classification Search
CPC . A61B 18/14; A61B 18/1442; A61B 18/1445; A61B 18/1448
USPC .................................................. 606/27–41
See application file for complete search history.

(56) References Cited

U.S. PATENT DOCUMENTS

| | | |
|---|---|---|
| 1,719,750 A | 9/1927 | Bridge et al. |
| 3,818,913 A | 6/1974 | Wallach |
| 3,871,374 A | 3/1975 | Bolduc et al. |
| 3,880,168 A | 4/1975 | Berman |
| 3,924,628 A | 12/1975 | Droegemueller et al. |
| 3,930,505 A | 1/1976 | Wallach |
| 4,024,866 A | 5/1977 | Wallach |
| 4,083,077 A | 4/1978 | Knight et al. |
| 4,447,227 A | 5/1984 | Kotsanis |
| 4,672,962 A | 6/1987 | Hershenson |
| 4,682,596 A | 7/1987 | Bales et al. |
| 4,748,979 A | 6/1988 | Hershenson |
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,941,475 A | 7/1990 | Williams et al. |
| 4,950,266 A | 8/1990 | Sinofsky |
| 4,976,711 A | 12/1990 | Parins et al. |
| 4,985,027 A | 1/1991 | Dressel |
| 5,006,119 A | 4/1991 | Acker et al. |
| 5,011,566 A | 4/1991 | Hoffman |
| 5,045,056 A | 9/1991 | Behl |
| 5,078,736 A | 1/1992 | Behl |
| 5,084,043 A | 1/1992 | Hertzmann et al. |
| 5,084,044 A | 1/1992 | Quint |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,218,970 A | 6/1993 | Turnbull et al. |
| 5,242,474 A | 9/1993 | Herbst et al. |
| 5,246,436 A | 9/1993 | Rowe |
| 5,263,951 A | 11/1993 | Spears et al. |
| 5,277,696 A | 1/1994 | Hagen |
| 5,298,298 A | 3/1994 | Hoffman |
| 5,306,274 A | 4/1994 | Long |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,437,629 A | 8/1995 | Goldrath |
| 5,443,470 A | 8/1995 | Stern et al. |
| 5,445,168 A | 8/1995 | Krebs |
| 5,449,380 A | 9/1995 | Chin |
| 5,451,208 A | 9/1995 | Goldrath |
| 5,462,521 A | 10/1995 | Brucker et al. |
| 5,500,012 A | 3/1996 | Brucker et al. |
| 5,503,638 A | 4/1996 | Cooper et al. |
| 5,505,730 A | 4/1996 | Edwards |
| 5,524,620 A | 6/1996 | Rosenschein |
| 5,529,076 A | 6/1996 | Schachar |
| 5,540,658 A | 7/1996 | Evans et al. |
| 5,542,928 A | 8/1996 | Evans et al. |
| 5,549,628 A | 8/1996 | Cooper et al. |
| 5,554,172 A | 9/1996 | Horner et al. |
| 5,562,608 A | 10/1996 | Sekins et al. |
| 5,562,720 A | 10/1996 | Stern et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,647,871 A | 7/1997 | Levine et al. |
| 5,653,692 A | 8/1997 | Masterson et al. |
| 5,662,671 A | 9/1997 | Barbut et al. |
| 5,665,074 A | 9/1997 | Kelly |
| 5,669,907 A | 9/1997 | Platt, Jr. et al. |
| 5,674,191 A | 10/1997 | Edwards et al. |
| 5,681,282 A | 10/1997 | Eggers et al. |
| 5,683,366 A | 11/1997 | Eggers et al. |
| 5,688,267 A | 11/1997 | Panescu et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,730,719 A | 3/1998 | Edwards |
| 5,735,811 A | 4/1998 | Brisken |
| 5,741,247 A | 4/1998 | Rizoiu et al. |
| 5,741,248 A | 4/1998 | Stern et al. |
| 5,743,870 A | 4/1998 | Edwards |
| 5,752,965 A | 5/1998 | Francis et al. |
| 5,754,717 A | 5/1998 | Esch |
| 5,755,753 A | 5/1998 | Knowlton |
| 5,769,880 A | 6/1998 | Truckai et al. |
| 5,782,914 A | 7/1998 | Schankereli |
| 5,785,521 A | 7/1998 | Rizoiu et al. |
| 5,800,379 A | 9/1998 | Edwards |
| 5,800,482 A | 9/1998 | Pomeranz et al. |
| 5,800,493 A | 9/1998 | Stevens et al. |
| 5,810,764 A | 9/1998 | Eggers et al. |
| 5,820,580 A | 10/1998 | Edwards et al. |
| 5,824,703 A | 10/1998 | Clark, Jr. |
| 5,827,268 A | 10/1998 | Laufer |
| 5,830,213 A | 11/1998 | Panescu et al. |
| 5,836,896 A | 11/1998 | Rosenschein |
| 5,836,906 A | 11/1998 | Edwards |
| 5,843,019 A | 12/1998 | Eggers et al. |
| 5,843,073 A | 12/1998 | Sinofsky |
| 5,871,469 A | 2/1999 | Eggers et al. |
| 5,873,855 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,911,734 A | 6/1999 | Tsugita et al. |
| 5,913,856 A | 6/1999 | Chia et al. |
| 5,938,660 A | 8/1999 | Swartz et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwin |
| 5,989,445 A | 11/1999 | Wise et al. |
| 5,997,499 A | 12/1999 | Sussman et al. |
| 6,004,509 A | 12/1999 | Dey et al. |
| 6,015,406 A | 1/2000 | Goble et al. |
| 6,024,095 A | 2/2000 | Stanley, III |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,045,532 A | 4/2000 | Eggers et al. |
| 6,045,549 A | 4/2000 | Smethers et al. |
| 6,047,700 A | 4/2000 | Eggers et al. |
| 6,053,172 A | 4/2000 | Hovda et al. |

(56) References Cited

U.S. PATENT DOCUMENTS

| | | |
|---|---|---|
| 6,053,909 A | 4/2000 | Shadduck |
| 6,056,746 A | 5/2000 | Goble et al. |
| 6,057,689 A | 5/2000 | Saadat |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,066,139 A | 5/2000 | Ryan et al. |
| 6,074,358 A | 6/2000 | Andrew et al. |
| 6,080,128 A | 6/2000 | Sussman et al. |
| 6,080,151 A | 6/2000 | Swartz et al. |
| 6,083,255 A | 7/2000 | Laufer et al. |
| 6,086,585 A | 7/2000 | Hovda et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,105,581 A | 8/2000 | Eggers et al. |
| 6,106,516 A | 8/2000 | Bmassengill |
| 6,109,268 A | 8/2000 | Thapliyal et al. |
| 6,110,162 A | 8/2000 | Sussman et al. |
| 6,113,597 A | 9/2000 | Eggers et al. |
| 6,113,722 A | 9/2000 | Hoffman et al. |
| 6,117,109 A | 9/2000 | Eggers et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,160 A | 12/2000 | Hsei et al. |
| 6,159,194 A | 12/2000 | Eggers et al. |
| 6,159,207 A | 12/2000 | Yoon |
| 6,159,208 A | 12/2000 | Hovda et al. |
| 6,162,232 A | 12/2000 | Shadduck |
| 6,168,594 B1 | 1/2001 | LaFontaine et al. |
| 6,174,308 B1 | 1/2001 | Goble et al. |
| 6,179,805 B1 | 1/2001 | Sussman et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,203,542 B1 | 3/2001 | Ellsberry et al. |
| 6,206,848 B1 | 3/2001 | Sussman et al. |
| 6,210,402 B1 | 4/2001 | Olsen et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,228,078 B1 | 5/2001 | Eggers et al. |
| 6,228,081 B1 | 5/2001 | Goble |
| 6,228,082 B1 | 5/2001 | Baker et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,254,600 B1 | 7/2001 | Willink et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,654 B1 | 7/2001 | Swartz et al. |
| 6,277,112 B1 | 8/2001 | Underwood et al. |
| 6,277,114 B1 | 8/2001 | Bullivant et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,299,633 B1 | 10/2001 | Laufer |
| 6,300,150 B1 | 10/2001 | Venkatasubramanian |
| 6,306,129 B1 | 10/2001 | Little et al. |
| 6,306,134 B1 | 10/2001 | Goble et al. |
| 6,309,387 B1 | 10/2001 | Eggers et al. |
| 6,312,408 B1 | 11/2001 | Eggers et al. |
| 6,312,474 B1 | 11/2001 | Francis et al. |
| 6,315,755 B1 | 11/2001 | Sussman |
| 6,319,221 B1 | 11/2001 | Savage et al. |
| 6,319,222 B1 | 11/2001 | Andrew et al. |
| 6,322,549 B1 | 11/2001 | Eggers et al. |
| 6,327,505 B1 | 12/2001 | Medhkour et al. |
| 6,328,735 B1 | 12/2001 | Curley et al. |
| 6,331,171 B1 | 12/2001 | Cohen |
| 6,355,032 B1 | 3/2002 | Hovda et al. |
| 6,361,531 B1 | 3/2002 | Hissong |
| 6,363,937 B1 | 4/2002 | Hovda et al. |
| 6,364,877 B1 | 4/2002 | Goble et al. |
| 6,375,635 B1 | 4/2002 | Moutafis et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,699 B1 | 6/2002 | Ash |
| 6,409,723 B1 | 6/2002 | Edwards |
| 6,416,507 B1 | 7/2002 | Eggers et al. |
| 6,416,508 B1 | 7/2002 | Eggers et al. |
| 6,416,509 B1 | 7/2002 | Goble et al. |
| 6,432,103 B1 | 8/2002 | Ellsberry et al. |
| 6,440,089 B1 | 8/2002 | Shine |
| 6,443,947 B1 | 9/2002 | Marko et al. |
| 6,458,231 B1 | 10/2002 | Wapner et al. |
| 6,461,350 B1 | 10/2002 | Underwood et al. |
| 6,461,354 B1 | 10/2002 | Olsen et al. |
| 6,464,694 B1 | 10/2002 | Massengil |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,475,215 B1 | 11/2002 | Tanrisever |
| 6,482,201 B1 | 11/2002 | Olsen et al. |
| 6,482,202 B1 | 11/2002 | Goble et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,510,854 B2 | 1/2003 | Goble |
| 6,517,533 B1 | 2/2003 | Swaminathan |
| 6,517,568 B1 | 2/2003 | Sharkey et al. |
| 6,522,930 B1 | 2/2003 | Schaer et al. |
| 6,527,761 B1 | 3/2003 | Soltesz et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,248 B1 | 4/2003 | Bass |
| 6,544,261 B2 | 4/2003 | Ellsberry et al. |
| 6,547,784 B1 | 4/2003 | Thompson et al. |
| 6,547,810 B1 | 4/2003 | Sharkey et al. |
| 6,551,271 B2 | 4/2003 | Nguyen |
| 6,551,274 B2 | 4/2003 | Heiner |
| 6,554,780 B1 | 4/2003 | Sampson et al. |
| 6,557,559 B1 | 5/2003 | Eggers et al. |
| 6,558,379 B1 | 5/2003 | Batchelor et al. |
| 6,565,561 B1 | 5/2003 | Goble et al. |
| 6,569,146 B1 | 5/2003 | Werner et al. |
| 6,575,929 B2 | 6/2003 | Sussman et al. |
| 6,575,933 B1 | 6/2003 | Wittenberger et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,204 B1 | 7/2003 | Sussman et al. |
| 6,589,237 B2 | 7/2003 | Woloszko et al. |
| 6,592,594 B2 | 7/2003 | Rimbaugh et al. |

(56) References Cited

U.S. PATENT DOCUMENTS

| | | |
|---|---|---|
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,605,087 B2 | 8/2003 | Swartz et al. |
| 6,610,043 B1 | 8/2003 | Ingenito |
| 6,620,130 B1 | 9/2003 | Ginsburg |
| 6,620,155 B2 | 9/2003 | Underwood et al. |
| 6,623,444 B2 | 9/2003 | Babaev |
| 6,626,855 B1 | 9/2003 | Weng et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,634,363 B1 | 10/2003 | Danek et al. |
| 6,648,847 B2 | 11/2003 | Sussman et al. |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,682,520 B2 | 1/2004 | Ingenito |
| 6,682,543 B2 | 1/2004 | Barbut et al. |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,708,056 B2 | 3/2004 | Duchon et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,723,064 B2 | 4/2004 | Babaev |
| 6,726,684 B1 | 4/2004 | Woloszko et al. |
| 6,726,708 B2 | 4/2004 | Lasheras |
| 6,746,447 B2 | 6/2004 | Davison et al. |
| 6,749,604 B1 | 6/2004 | Eggers et al. |
| 6,755,794 B2 | 6/2004 | Soukup |
| 6,758,846 B2 | 7/2004 | Goble et al. |
| 6,763,836 B2 | 7/2004 | Tasto et al. |
| 6,764,487 B2 | 7/2004 | Mulier et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,813,520 B2 | 11/2004 | Truckai et al. |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B1 | 3/2005 | Sussman et al. |
| 6,875,194 B2 | 4/2005 | MacKool |
| 6,896,672 B1 | 5/2005 | Eggers et al. |
| 6,896,674 B1 | 5/2005 | Woloszko et al. |
| 6,896,675 B2 | 5/2005 | Leung et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,915,806 B2 | 7/2005 | Pacek et al. |
| 6,918,903 B2 | 7/2005 | Bass |
| 6,921,385 B2 | 7/2005 | Clements et al. |
| 6,929,640 B1 | 8/2005 | Underwood et al. |
| 6,929,642 B2 | 8/2005 | Xiao et al. |
| 6,949,096 B2 | 9/2005 | Davison et al. |
| 6,955,675 B2 | 10/2005 | Jain |
| 6,960,182 B2 | 11/2005 | Moutafis et al. |
| 6,960,204 B2 | 11/2005 | Eggers et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |
| 6,991,028 B2 | 1/2006 | Comeaux et al. |
| 6,991,631 B2 | 1/2006 | Woloszko et al. |
| 7,004,940 B2 | 2/2006 | Ryan et al. |
| 7,004,941 B2 | 2/2006 | Tvinnereim et al. |
| 7,022,088 B2 | 4/2006 | Keast et al. |
| 7,031,504 B1 | 4/2006 | Argiro et al. |
| 7,070,596 B1 | 7/2006 | Woloszko et al. |
| 7,083,612 B2 | 8/2006 | Littrup et al. |
| 7,094,215 B2 | 8/2006 | Davison et al. |
| 7,094,249 B1 | 8/2006 | Broome et al. |
| 7,101,367 B2 | 9/2006 | Xiao et al. |
| 7,104,986 B2 | 9/2006 | Hovda et al. |
| 7,105,007 B2 | 9/2006 | Hibler |
| 7,128,748 B2 | 10/2006 | Mooradian et al. |
| 7,131,969 B1 | 11/2006 | Hovda et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,162,303 B2 | 1/2007 | Levin et al. |
| 7,169,143 B2 | 1/2007 | Eggers et al. |
| 7,179,255 B2 | 2/2007 | Lettice et al. |
| 7,186,234 B2 | 3/2007 | Dahla et al. |
| 7,192,400 B2 | 3/2007 | Campbell et al. |
| 7,192,428 B2 | 3/2007 | Eggers et al. |
| 7,201,750 B1 | 4/2007 | Eggers et al. |
| 7,217,268 B2 | 5/2007 | Eggers et al. |
| 7,233,820 B2 | 6/2007 | Gilboa |
| 7,235,070 B2 | 6/2007 | Vanney |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,297,143 B2 | 11/2007 | Woloszko et al. |
| 7,297,145 B2 | 11/2007 | Woloszko et al. |
| 7,311,708 B2 | 12/2007 | McClurken |
| 7,320,325 B2 | 1/2008 | Duchon et al. |
| 7,335,195 B2 | 2/2008 | Mehier |
| 7,347,859 B2 | 3/2008 | Garabedian et al. |
| 7,524,315 B2 | 4/2009 | Blott et al. |
| 7,549,987 B2 | 6/2009 | Shadduck |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,674,259 B2 | 3/2010 | Shadduck |
| 7,717,948 B2 | 5/2010 | Demarais et al. |
| 7,756,583 B2 | 7/2010 | Demarais et al. |
| 7,815,616 B2 | 10/2010 | Boehringer et al. |
| 7,815,646 B2 | 10/2010 | Hart |
| 7,853,333 B2 | 12/2010 | Demarais |
| 7,873,417 B2 | 1/2011 | Demarais et al. |
| 7,892,229 B2 | 2/2011 | Shadduck et al. |
| 7,937,143 B2 | 5/2011 | Demarais et al. |
| 7,993,323 B2 | 8/2011 | Barry et al. |
| 8,016,823 B2 | 9/2011 | Shadduck |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,269 B2 | 5/2012 | Shadduck et al. |
| 8,182,424 B2 | 6/2012 | Woloszko |
| 8,197,470 B2 | 6/2012 | Sharkey et al. |
| 8,216,217 B2 | 7/2012 | Sharkey et al. |
| 8,221,401 B2 | 7/2012 | Sharkey et al. |
| 8,221,403 B2 | 7/2012 | Sharkey et al. |
| 8,313,485 B2 | 11/2012 | Shadduck |
| 8,444,636 B2 | 5/2013 | Shadduck et al. |

(56) References Cited

U.S. PATENT DOCUMENTS

| | | | |
|---|---|---|---|
| 8,574,226 B2 | 11/2013 | Shadduck | |
| 8,579,888 B2 | 11/2013 | Hoey et al. | |
| 8,579,892 B2 | 11/2013 | Hoey et al. | |
| 8,579,893 B2 | 11/2013 | Hoey | |
| 8,585,645 B2 | 11/2013 | Barry et al. | |
| 8,721,632 B2 | 5/2014 | Hoey et al. | |
| 8,858,549 B2 | 10/2014 | Shadduck et al. | |
| 8,900,223 B2 | 12/2014 | Shadduck | |
| 8,911,430 B2 | 12/2014 | Hoey et al. | |
| 9,113,944 B2 | 8/2015 | Shadduck | |
| 9,161,801 B2 | 10/2015 | Hoey | |
| 9,204,889 B2 | 12/2015 | Shadduck | |
| 9,433,457 B2 | 9/2016 | Shadduck | |
| 9,468,487 B2 | 10/2016 | Shadduck et al. | |
| 9,615,875 B2 | 4/2017 | Shadduck | |
| 9,662,060 B2 | 5/2017 | Peliks et al. | |
| 9,700,365 B2 | 7/2017 | Sharma | |
| 9,743,974 B2 | 8/2017 | Gurskis et al. | |
| 9,907,599 B2 | 3/2018 | Hoey et al. | |
| 9,924,992 B2 | 3/2018 | Hoey | |
| 9,943,353 B2 | 4/2018 | Hoey et al. | |
| 9,993,290 B2 | 6/2018 | Chee et al. | |
| 10,499,973 B2 | 12/2019 | Hoey et al. | |
| 10,524,847 B2 | 1/2020 | Shadduck | |
| 10,548,653 B2 | 2/2020 | Hoey et al. | |
| 10,595,925 B2 | 3/2020 | Hoey et al. | |
| 10,842,557 B2 | 11/2020 | Sharma et al. | |
| 11,129,664 B2 | 9/2021 | Shadduck et al. | |
| 11,141,210 B2 | 10/2021 | Shadduck | |
| 11,179,187 B2 | 11/2021 | Shadduck et al. | |
| 2001/0020167 A1 | 9/2001 | Woloszko et al. | |
| 2001/0029370 A1 | 10/2001 | Hodva et al. | |
| 2001/0037106 A1 | 11/2001 | Shadduck | |
| 2002/0007180 A1 | 1/2002 | Wittenberger et al. | |
| 2002/0013601 A1 | 1/2002 | Nobles et al. | |
| 2002/0019627 A1 | 2/2002 | Maguire et al. | |
| 2002/0049438 A1 | 4/2002 | Sharkey et al. | |
| 2002/0077516 A1 | 6/2002 | Flanigan | |
| 2002/0078956 A1 | 6/2002 | Sharpe et al. | |
| 2002/0082667 A1 | 6/2002 | Shadduck | |
| 2002/0095152 A1 | 7/2002 | Ciarrocca et al. | |
| 2002/0111386 A1 | 8/2002 | Sekins et al. | |
| 2002/0128638 A1 | 9/2002 | Chauvet et al. | |
| 2002/0133147 A1 | 9/2002 | Marchitto et al. | |
| 2002/0151917 A1 | 10/2002 | Barry | |
| 2002/0161326 A1 | 10/2002 | Sussman et al. | |
| 2002/0161362 A1* | 10/2002 | Penny | H05H 1/24 606/41 |
| 2002/0173815 A1 | 11/2002 | Hogendijk et al. | |
| 2002/0177846 A1 | 11/2002 | Mulier et al. | |
| 2002/0193789 A1 | 12/2002 | Underwood et al. | |
| 2003/0028189 A1 | 2/2003 | Woloszko et al. | |
| 2003/0040742 A1 | 2/2003 | Underwood et al. | |
| 2003/0097126 A1 | 5/2003 | Woloszko et al. | |
| 2003/0097129 A1 | 5/2003 | Davison et al. | |
| 2003/0099279 A1 | 5/2003 | Venkatasubramanian et al. | |
| 2003/0109869 A1 | 6/2003 | Shadduck | |
| 2003/0130655 A1 | 7/2003 | Woloszko et al. | |
| 2003/0130738 A1 | 7/2003 | Hovda et al. | |
| 2003/0144654 A1 | 7/2003 | Hilal | |
| 2003/0153905 A1 | 8/2003 | Edwards et al. | |
| 2003/0158545 A1 | 8/2003 | Hovda et al. | |
| 2003/0163178 A1 | 8/2003 | Davison et al. | |
| 2003/0181922 A1 | 9/2003 | Alferness | |
| 2003/0212394 A1 | 11/2003 | Pearson et al. | |
| 2003/0212395 A1 | 11/2003 | Woloszko et al. | |
| 2003/0217962 A1 | 11/2003 | Childers et al. | |
| 2003/0220604 A1 | 11/2003 | Al-Anazi | |
| 2003/0225364 A1 | 12/2003 | Kraft et al. | |
| 2004/0002698 A1 | 1/2004 | Hua Xiao et al. | |
| 2004/0024398 A1 | 2/2004 | Hovda et al. | |
| 2004/0024399 A1 | 2/2004 | Sharps et al. | |
| 2004/0031494 A1 | 2/2004 | Danek et al. | |
| 2004/0038868 A1 | 2/2004 | Ingenito | |
| 2004/0047855 A1 | 3/2004 | Ingenito | |
| 2004/0049180 A1 | 3/2004 | Sharps et al. | |
| 2004/0054366 A1 | 3/2004 | Davison et al. | |
| 2004/0055606 A1 | 3/2004 | Hendricksen et al. | |
| 2004/0068256 A1 | 4/2004 | Rizoiu et al. | |
| 2004/0068306 A1 | 4/2004 | Shadduck | |
| 2004/0087937 A1 | 5/2004 | Eggers et al. | |
| 2004/0116922 A1 | 6/2004 | Hovda et al. | |
| 2004/0193150 A1 | 9/2004 | Sharkey et al. | |
| 2004/0199226 A1 | 10/2004 | Shadduck | |
| 2004/0230190 A1 | 11/2004 | Dahla et al. | |
| 2004/0254532 A1 | 12/2004 | Mehier | |
| 2005/0004634 A1 | 1/2005 | Ricart et al. | |
| 2005/0010205 A1 | 1/2005 | Hovda et al. | |
| 2005/0070894 A1 | 3/2005 | McClurken | |
| 2005/0119650 A1 | 6/2005 | Sanders et al. | |
| 2005/0143728 A1 | 6/2005 | Sampson et al. | |
| 2005/0166925 A1 | 8/2005 | Wilson et al. | |
| 2005/0171574 A1 | 8/2005 | Rubinsky et al. | |
| 2005/0171582 A1 | 8/2005 | Matlock | |
| 2005/0177147 A1 | 8/2005 | Vancelette et al. | |
| 2005/0187543 A1 | 8/2005 | Underwood et al. | |
| 2005/0215991 A1 | 9/2005 | Altman et al. | |
| 2005/0222485 A1 | 10/2005 | Shaw et al. | |
| 2005/0228423 A1 | 10/2005 | Khashayar et al. | |
| 2005/0228424 A1 | 10/2005 | Khashayar et al. | |
| 2005/0240171 A1 | 10/2005 | Forrest | |
| 2005/0240239 A1 | 10/2005 | Boveja et al. | |
| 2005/0267467 A1* | 12/2005 | Paul et al. | 606/41 |
| 2005/0267468 A1 | 12/2005 | Truckai et al. | |
| 2005/0283143 A1 | 12/2005 | Rizoiu | |
| 2006/0004400 A1 | 1/2006 | McGurk et al. | |
| 2006/0047291 A1 | 3/2006 | Barry | |
| 2006/0058831 A1 | 3/2006 | Atad | |
| 2006/0085054 A1 | 4/2006 | Zikorus et al. | |
| 2006/0100619 A1 | 5/2006 | McClurken et al. | |
| 2006/0130830 A1 | 6/2006 | Barry | |
| 2006/0135955 A1 | 6/2006 | Shadduck | |
| 2006/0142783 A1 | 6/2006 | Lewis et al. | |
| 2006/0161147 A1* | 7/2006 | Privitera | A61B 18/1402 606/34 |
| 2006/0161233 A1 | 7/2006 | Barry et al. | |
| 2006/0200076 A1 | 9/2006 | Gonzalez et al. | |
| 2006/0206150 A1 | 9/2006 | Demarais et al. | |
| 2006/0224154 A1 | 10/2006 | Shadduck et al. | |
| 2006/0265053 A1 | 11/2006 | Hunt | |
| 2006/0271111 A1 | 11/2006 | Demarais et al. | |
| 2007/0021713 A1 | 1/2007 | Kumar et al. | |
| 2007/0032785 A1 | 2/2007 | Diederich et al. | |
| 2007/0036417 A1 | 2/2007 | Argiro et al. | |
| 2007/0066990 A1 | 3/2007 | Marsella et al. | |
| 2007/0091087 A1 | 4/2007 | Zuiderveld | |
| 2007/0129720 A1 | 6/2007 | Demarais et al. | |
| 2007/0129760 A1 | 6/2007 | Demarais et al. | |
| 2007/0129761 A1 | 6/2007 | Demarais et al. | |
| 2007/0135875 A1 | 6/2007 | Demarais et al. | |
| 2007/0225744 A1 | 9/2007 | Nobles et al. | |
| 2007/0239197 A1 | 10/2007 | Dubey et al. | |
| 2007/0265687 A1 | 11/2007 | Deem et al. | |
| 2007/0288051 A1 | 12/2007 | Beyer et al. | |
| 2008/0033493 A1 | 2/2008 | Deckman et al. | |
| 2008/0077201 A1 | 3/2008 | Levinson et al. | |
| 2008/0097429 A1 | 4/2008 | McClurken | |
| 2008/0103566 A1 | 5/2008 | Mehier | |
| 2008/0110457 A1 | 5/2008 | Barry et al. | |
| 2008/0114297 A1 | 5/2008 | Barry et al. | |
| 2008/0125747 A1 | 5/2008 | Prokop | |
| 2008/0132826 A1 | 6/2008 | Shadduck et al. | |
| 2008/0135053 A1 | 6/2008 | Gruber et al. | |
| 2008/0161788 A1 | 7/2008 | Dando et al. | |
| 2008/0167664 A1 | 7/2008 | Payne et al. | |
| 2008/0213331 A1 | 9/2008 | Gelfand et al. | |
| 2008/0249467 A1 | 10/2008 | Burnett et al. | |
| 2008/0255642 A1 | 10/2008 | Zarins et al. | |
| 2009/0012512 A1 | 1/2009 | Utley et al. | |
| 2009/0024108 A1 | 1/2009 | Lee-Sepsick et al. | |
| 2009/0030412 A1 | 1/2009 | Willis et al. | |
| 2009/0036948 A1 | 2/2009 | Levin et al. | |
| 2009/0054871 A1 | 2/2009 | Sharkey et al. | |
| 2009/0062873 A1 | 3/2009 | Wu et al. | |

(56) References Cited

U.S. PATENT DOCUMENTS

| | | |
|---|---|---|
| 2009/0076409 A1 | 3/2009 | Wu et al. |
| 2009/0105702 A1 | 4/2009 | Shadduck |
| 2009/0105703 A1 | 4/2009 | Shadduck |
| 2009/0125009 A1 | 5/2009 | Zikorus et al. |
| 2009/0125010 A1 | 5/2009 | Sharkey et al. |
| 2009/0149846 A1 | 6/2009 | Hoey et al. |
| 2009/0216220 A1 | 8/2009 | Hoey et al. |
| 2009/0306640 A1 | 12/2009 | Glaze et al. |
| 2009/0312753 A1 | 12/2009 | Shadduck |
| 2010/0076416 A1 | 3/2010 | Hoey et al. |
| 2010/0094268 A1* | 4/2010 | Bouthillier ............ A61B 18/04 606/27 |
| 2010/0094270 A1 | 4/2010 | Sharma |
| 2010/0114083 A1 | 5/2010 | Sharma |
| 2010/0137860 A1 | 6/2010 | Demarais et al. |
| 2010/0137952 A1 | 6/2010 | Demarais et al. |
| 2010/0160905 A1 | 6/2010 | Shadduck |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |
| 2010/0185189 A1 | 7/2010 | Hoey |
| 2010/0191112 A1 | 7/2010 | Demarais et al. |
| 2010/0204688 A1 | 8/2010 | Hoey et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2010/0286679 A1 | 11/2010 | Hoey et al. |
| 2011/0060324 A1 | 3/2011 | Wu et al. |
| 2011/0077628 A1 | 3/2011 | Hoey et al. |
| 2011/0112400 A1 | 5/2011 | Emery et al. |
| 2011/0118717 A1 | 5/2011 | Shadduck |
| 2011/0144630 A1 | 6/2011 | Loeb |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel |
| 2011/0202098 A1 | 8/2011 | Demarais et al. |
| 2011/0208096 A1 | 8/2011 | Demarais et al. |
| 2011/0238144 A1 | 9/2011 | Hoey et al. |
| 2011/0257564 A1 | 10/2011 | Demarais et al. |
| 2011/0257641 A1 | 10/2011 | Hastings et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0172837 A1 | 7/2012 | Demarais et al. |
| 2012/0197198 A1 | 8/2012 | Demarais et al. |
| 2012/0197252 A1 | 8/2012 | Deem et al. |
| 2012/0259271 A1 | 10/2012 | Shadduck et al. |
| 2012/0283717 A1 | 11/2012 | Sharkey et al. |
| 2013/0079772 A1 | 3/2013 | Shadduck |
| 2013/0116683 A1 | 5/2013 | Shadduck et al. |
| 2013/0178910 A1 | 7/2013 | Azamian et al. |
| 2013/0237978 A1 | 9/2013 | Shadduck et al. |
| 2014/0018890 A1 | 1/2014 | Hoey et al. |
| 2014/0025057 A1 | 1/2014 | Hoey et al. |
| 2014/0031805 A1 | 1/2014 | Shadduck |
| 2014/0088581 A1 | 3/2014 | Kelly et al. |
| 2014/0200569 A1 | 7/2014 | Shadduck |
| 2014/0200570 A1 | 7/2014 | Hoey et al. |
| 2014/0276713 A1 | 9/2014 | Hoey et al. |
| 2014/0316398 A1 | 10/2014 | Kelly et al. |
| 2014/0324037 A1 | 10/2014 | Hoey et al. |
| 2015/0025515 A1 | 1/2015 | Hoey et al. |
| 2015/0335373 A1 | 11/2015 | Chee et al. |
| 2017/0172641 A1 | 6/2017 | Shadduck |
| 2017/0258511 A1 | 9/2017 | Peliks et al. |
| 2017/0354452 A1 | 12/2017 | Gurskis et al. |
| 2018/0168713 A1 | 6/2018 | Hoey et al. |
| 2018/0193079 A1 | 7/2018 | Hoey et al. |
| 2018/0199982 A1 | 7/2018 | Hoey et al. |
| 2019/0117289 A1 | 4/2019 | Sharkey et al. |
| 2019/0117290 A1 | 4/2019 | Sharkey et al. |
| 2019/0216523 A1 | 7/2019 | Gurskis et al. |
| 2020/0078073 A1 | 3/2020 | Hoey et al. |
| 2020/0188008 A1 | 6/2020 | Hoey et al. |
| 2021/0186586 A1 | 6/2021 | Shadduck et al. |
| 2021/0204993 A1 | 7/2021 | Shadduck et al. |
| 2021/0212746 A1 | 7/2021 | Shadduck |
| 2021/0212747 A1 | 7/2021 | Shadduck |

FOREIGN PATENT DOCUMENTS

| | | |
|---|---|---|
| WO | WO 2002/069821 | 9/2002 |
| WO | WO 2003/070302 | 8/2003 |
| WO | WO 2003/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

Fishman et al., "A randomized trial comparing lung-volume-reduction surgery with medical therapy for severe emphysema," *N Engl J Med*, vol. 348, No. 21, pp. 2059-2073, May 22, 2003.

Homasson, et al., "Bronchoscopic cryotherapy for airway strictures caused by tumors," *Chest*, vol. 90, No. 2, pp. 159-164, Aug. 1986.

Li, K., "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," *Chest*, vol. 103, No. 2, pp. 472-474, Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723, Sep. 1996.

Morice et al. "Endobrinchial argon plasma coagulation for treatment of hemotysis and neoplastic airway obstruction," *Chest*, vol. 119, No. 3, pp. 781-787, Mar. 2001.

Moulding et al., "Preliminary studies for achieving transcervical oviduct occlusion by hot water or low-pressure steam," *Advancesin Planned Parenthood*, vol. 12, No. 2; pp. 79-85, 1977.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp. 1-17, 1994.

Tschirren et al.; "Intrathoracic airway trees: segmentation and airway morphology analysis from low-dose CT scans;" *IEEE Trans. Med. Imaging*, vol. 24, No. 12; pp. 1529-1539, Dec. 2005.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

(56) References Cited

OTHER PUBLICATIONS

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Unger, M. et al. "Monolithic Microfabricated Valves and Pumps by Multilayer Soft Lithography," *Science,* vol. 288, pp. 113-116, Apr. 7, 2000, accessed at http://web.mit.edu/thorsen/www/113.pdf.

Xia, Y. et al. "Sof Lithography," *Annu. Rev. Mater. Sci.,* vol. 28, pp. 153-184, 1998, accessed at http://www.bwfoundry.com/xia.pdf.

\* cited by examiner

MEDICAL SYSTEMS AND METHODS FOR ABLATING AND ABSORBING TISSUE

CROSS-REFERENCE TO RELATED APPLICATIONS

This application is a non-provisional of U.S. Provisional Application No.: 61/206,823 filed Feb. 3, 2009, the entirely of which is incorporated by reference herein.

This application is related to the following Patent Applications: PCT/US2008/069094 filed Jul. 2, 2008 titled "Medical System and Method of Use"; Ser. No. 10/681,625 filed Oct. 7, 2003 titled "Medical Instruments and Techniques for Thermally-Mediated Therapies"; Ser. No. 11/158,930 filed Jun. 22, 2005 titled "Medical Instruments and Techniques for Treating Pulmonary Disorders"; Ser. No. 11/244,329 filed Oct. 5, 2005 titled "Medical Instruments and Methods of Use" and Ser. No. 11/329,381 filed Jan. 10, 2006 titled "Medical Instrument and Method of Use". All of the above applications are incorporated herein by this reference and made a part of this specification, together with the specifications of all other commonly-invented applications cited in the above applications.

FIELD OF THE INVENTION

This invention relates to medical instruments and systems for applying energy to tissue, and more particularly relates to a system for ablating, sealing, welding, coagulating, shrinking or creating lesions in tissue by means of contacting a targeted site in a patient with a vapor phase media wherein a subsequent vapor-to-liquid phase change of the media applies thermal energy to the tissue to cause an intended therapeutic effect. Variations of the invention include devices and methods for monitoring the vapor flow for various parameters with one or more sensors. In yet additional variations, the invention includes devices and methods for modulating parameters of the system in response to the observed parameters.

BACKGROUND OF THE INVENTION

Various types of medical instruments utilizing radiofrequency (Rf) energy, laser energy, microwave energy and the like have been developed for delivering thermal energy to tissue, for example to ablate tissue. While such prior art forms of energy delivery work well for some applications, Rf, laser and microwave energy typically cannot cause highly "controlled" and "localized" thermal effects that are desirable in controlled ablation soft tissue for ablating a controlled depth or for the creation of precise lesions in such tissue. In general, the non-linear or non-uniform characteristics of tissue affect electromagnetic energy distributions in tissue.

What is needed are systems and methods that controllably apply thermal energy in a controlled and localized manner without the lack of control often associated when Rf, laser and microwave energy are applied directly to tissue.

SUMMARY OF THE INVENTION

The present invention is adapted to provide improved methods of controlled thermal energy delivery to localized tissue volumes, for example for ablating, sealing, coagulating or otherwise damaging targeted tissue, for example to ablate a lesion interstitially or to ablate the lining of a body cavity. Of particular interest, the method causes thermal effects in targeted tissue without the use of Rf current flow through the patient's body and without the potential of carbonizing tissue.

In general, the thermally-mediated treatment method comprises causing a vapor-to-liquid phase state change in a selected media at a targeted tissue site thereby applying thermal energy substantially equal to the heat of vaporization of the selected media to the tissue site. The thermally-mediated therapy can be delivered to tissue by such vapor-to-liquid phase transitions, or "internal energy" releases, about the working surfaces of several types of instruments for ablative treatments of soft tissue. FIGS. 1A and 1B illustrate the phenomena of phase transitional releases of internal energies. Such internal energy involves energy on the molecular and atomic scale—and in polyatomic gases is directly related to intermolecular attractive forces, as well as rotational and vibrational kinetic energy. In other words, the method of the invention exploits the phenomenon of internal energy transitions between gaseous and liquid phases that involve very large amounts of energy compared to specific heat.

It has been found that the controlled application of such energy in a controlled media-tissue interaction solves many of the vexing problems associated with energy-tissue interactions in Rf, laser and ultrasound modalities. The apparatus of the invention provides a vaporization chamber in the interior of an instrument, in a source remote from the instrument and/or in an instrument working end. A source provides liquid media to the interior vaporization chamber wherein energy is applied to create a selected volume of vapor media. In the process of the liquid-to-vapor phase transition of a liquid media, for example water, large amounts of energy are added to overcome the cohesive forces between molecules in the liquid, and an additional amount of energy is required to expand the liquid 1000+ percent (PAD) into a resulting vapor phase (see FIG. 1A). Conversely, in the vapor-to-liquid transition, such energy will be released at the phase transition at the interface with the targeted tissue site. That is, the heat of vaporization is released at the interface when the media transitions from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy at the interface with the targeted body structure. Heat flow and work are both ways of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calorics/gm blocks) to elevate the temperature of water through its phase change to a vapor phase, the additional energy required to achieve the phase change (latent heat of vaporization) is represented by the large number of 110+ blocks of energy at 100° C. in FIG. 1A. Still referring to FIG. 1A, it can be easily understood that all other prior art ablation modalities—Rf, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present invention. The system provides for insulative containment of an initial primary energy-media interaction within an interior vaporization chamber of medical thermotherapy system. The initial, ascendant energy-media interaction delivers energy sufficient to achieve the heat of vaporization of a selected liquid media, such as water or saline solution, within an interior of the system. This aspect of the technology requires a highly controlled energy source wherein a computer controller may need to modulated energy application between very large energy densities to initially surpass the latent heat of vaporization with some energy sources (e.g. a resistive heat source, an Rf energy source, a light energy source, a microwave energy source, an ultrasound source and/or an inductive heat source) and potential subsequent lesser energy densities for maintaining a high vapor quality. Additionally, controller must control the pressure of liquid flows for replenishing the selected liquid media at the required rate and optionally for controlling propagation velocity of the vapor phase media from the working end surface of the instrument. In use, the method of the invention comprises the controlled application of energy to achieve the heat of vaporization as in FIG. 1A and the controlled vapor-to-liquid phase transition and vapor exit pressure to thereby control the interaction of a selected volume of vapor at the interface with tissue. The vapor-to-liquid phase transition can deposit 400, 500, 600 or more cal/gram within the targeted tissue site to perform the thermal ablation with the vapor in typical pressures and temperatures.

In one variation, the present disclosure includes medical systems for applying thermal energy to tissue, where the system comprises an elongated probe with an axis having an interior flow channel extending to at least one outlet in a probe working end; a source of vapor media configured to provide a vapor flow through at least a portion of the interior flow channel, wherein the vapor has a minimum temperature of; and at least one sensor in the flow channel for providing a signal of at least one flow parameter selected from the group one of (i) existence of a flow of the vapor media, (ii) quantification of a flow rate of the vapor media, and (iii) quality of the flow of the vapor media. The medical system can include variations where the minimum temperature varies from at least 80° C., 100° C. 120° C., 140° C. and 160° C. However, other temperature ranges can be included depending upon the desired application Sensors included in the above system include temperature sensor, an impedance sensor, a pressure sensor as well as an optical sensor.

In many variations, the devices and method described herein will include a visualization element placed within or adjacent to the treatment area. In many cases, the visualization element shall be coupled to a treatment device (either by being placed within the device or otherwise attached to the device. Any number of visualization elements can be incorporated with the methods and devices described herein. For example, a visualization element can include an optic fiber advanced within or adjacent to the device, a CCD camera affixed to the device or other visualization means as commonly used in remote visualization applications. The visualization element can provide imaging before, during, and/or after the controlled flow egresses from the device. In addition, the visualization element can include thermal imaging capabilities to monitor the vapor flow from the device or the treatment effect in tissue.

The source of vapor media can include a pressurized source of a liquid media and an energy source for phase conversion of the liquid media to a vapor media. In addition, the medical system can further include a controller capable of modulating a vapor parameter in response to a signal of a flow parameter; the vapor parameter selected from the group of (i) flow rate of pressurized source of liquid media, (ii) inflow pressure of the pressurized source of liquid media, (iii) temperature of the liquid media, (iv) energy applied from the energy source to the liquid media, (v) flow rate of vapor media in the flow channel, (vi) pressure of the vapor media in the flow channel, (vi) temperature of the vapor media, and (vii) quality of vapor media.

In another variation, a novel medical system for applying thermal energy to tissue comprises an elongated probe with an axis having an interior flow channel extending to at least one outlet in a probe working end, wherein a wall of the flow channel includes an insulative portion having a thermal conductivity of less than a maximum thermal conductivity; and a source of vapor media configured to provide a vapor flow through at least a portion of the interior flow channel, wherein the vapor has a minimum temperature Variations of such systems include systems where the maximum thermal conductivity ranges from 0.05 W/mK, 0.01 W/mK and 0.005 W/mK.

Another variation of a novel medical system for delivering energy to tissue comprises an elongated probe with a flow channel extending from a proximal portion of the probe to at least one flow outlet in an expandable working end; a source of a vapor flow in communication with the flow channel; and a recirculation channel having a distal end communicating with the working end.

The present disclosure also includes methods for applying energy to mammalian body structure, comprising providing an elongated probe with a distal working end and providing a pressure sensing mechanism for measuring pressure within at least one of the probe and the body structure; providing a flow of a non-ionized flow media from at least one port in the working end thereby applying energy to the body structure; and adjusting the pressure of the flow of the non-ionized flow media from the at least one port in response to a measured change in pressure by the pressure sensing mechanism.

In an additional variation, the inventive methods include a method of providing a therapeutic effect in a mammalian subject comprising providing a vapor source comprising a pressure source configured for providing a flow of liquid media from a liquid media source into a vaporization chamber having a heating mechanism; actuating the pump to provide the liquid into the vaporization chamber; applying energy from the heating mechanism to convert a substantially water media into a minimum water vapor; and introducing said vapor into an interface with tissue to cause the intended effect. While any range of water vapor can be included within the scope of this invention, variations include a minimum water vapor can range from 60% water vapor, 70% water vapor, 80% water vapor and 90% water vapor:

One embodiment of the invention comprises a system and method for delivering ablative energy to a body lumen or cavity, for example in an endometrial ablation procedure. One embodiment comprises an elongated probe with an insulated rigid or flexible shaft with a distal working end and a source of a vapor media that can be ejected from at least one outlet in the working end. The introduction and condensation of the vapor media is utilized to apply a selected level of thermal energy to ablate a surface portion of the body cavity. The method includes providing a vapor media capable of releasing the heat of vaporization, in one example, for global endometrial ablation. The method includes introducing the vapor media at a flow rate of ranging from 0.001 to 20 ml/min, 0.010 to 10 ml/min, 0.050 to 5 ml/min., at an inflow pressure ranging from 0.5 to 1000 psi, 5 to 500 psi, and 25 to 200 psi. The method includes applying the selected level of thermal energy over an interval ranging from 0.1 to 600 seconds; 0.5 to 300 seconds, and 1 to 180 seconds. Further, the application of energy may be pulsed as a suitable pulse rate. The system and method further include providing a controller for controlling the pressure in a body cavity, such as a uterine cavity.

The systems and probes of the invention are configured for controlled application of the heat of vaporization of a vapor-to liquid phase transition in an interface with tissue for tissue ablation, tissue sealing, tissue welding, and causing an immune response. In general, the instrument and method of the invention cause thermal ablations rapidly, efficiently and uniformly over a tissue interface.

The instrument and method of the invention generate vapor phase media that is controllable as to volume and ejection pressure to provide a not-to-exceed temperature level that prevents desiccation, eschar, smoke and tissue sticking.

The instrument and method of the invention cause an energy-tissue interaction that is imageable with intra-operative ultrasound or MRI.

The instrument and method of the invention cause thermal effects in tissue that do not rely on applying an electrical field across the tissue to be treated.

The instruments and methods described herein also provide for methods of applying energy to a region of tissue to cause resorption of the tissue by a body. In one example, such a method includes applying energy to the region of tissue for an activation time where the energy is uniformly delivered to prevent regions of high energy density in the region of tissue, controlling the energy delivery such that the region of tissue remains below a target temperature where the target temperature is dependent upon the activation time of the energy and is sufficient to ablate the region of tissue without causing a transformation of the region of tissue, where transformation of the tissue prevents eventual resorption of at least a portion of the region of tissue.

As noted herein, resorption of the tissue can comprise destruction, disappearance, and or dissolution of the region of tissue by a natural biochemical activity of the body.

In one variation, controlling the energy delivery includes controlling energy delivery such that the region of tissue remains below the target temperature comprises controlling the energy delivery such that the region of tissue remains below a heat fixation temperature, where the heat fixation temperature is dependent upon the activation time of the energy.

Applying energy can comprise delivering a vapor media to the region of tissue where upon contacting the region of tissue energy transfer occurs from the vapor media and the tissue. In one example, where controlling the energy delivery occurs such that the region of tissue remains below the target temperature comprises controlling a temperature of the vapor media.

As noted herein, and in the applications and patents cited herein, applying energy to the region of tissue can comprise inserting an energy delivery device into the body to the region of tissue.

Another variation of a method for ablating a region of tissue can include providing an energy supply that delivers energy in a uniform manner to the region of tissue such that the energy does not contain any regions of high energy density; controlling the energy supply to deliver energy to the region of tissue to increase a treatment temperature of tissue where the treatment temperature is sufficiently high to cause ablation of the region of tissue but insufficient to cause a fixation transformation of the treated tissue, where the fixation transformation prevents resorption of at least a portion of the region of tissue.

In another variation, the method includes applying energy to a region of tissue to cause resorption of the tissue by the body. In such a case, the method can include producing a vapor media by applying an amount of energy to a fluid media; directing the vapor media to the region of tissue for a treatment time, where the vapor media delivers energy uniformly within the region of tissue such that a temperature of the region of tissue rises above an ablation temperature, where the ablation temperature is dependent upon the treatment time; controlling the amount of energy applied to the fluid media such that the temperature of the region of tissue remains below a transformation temperature, where exceeding the transformation temperature causes transformation of a portion of the region of tissue and prevents resorption of at least some of the region tissue, where the transformation temperature is dependent upon the treatment time.

Systems and devices are also included for ablating tissue that can eventually be resorbed. In one example such a system includes a fluid media source; a fluid delivery device coupled to the fluid media source, where the fluid delivery device is configured to apply a vaporization energy to the fluid media and where the vaporization energy exceeds a heat of vaporization of the fluid media therein to convert the fluid media to a vapor media, where the fluid delivery device comprises at least one vapor delivery port to direct the vapor media to the tissue such that when the vapor media contacts the tissue energy transfer occurs from the vapor media to the tissue;

a controller coupled to the fluid delivery device, where the controller is configured to controlling delivery of the vaporization energy to maintain a treatment temperature of the tissue above an ablation temperature of the tissue and below a transformation temperature of the tissue, such that the energy ablates the tissue allowing the tissue to subsequently be resorbed by the body.

Additional advantages of the invention will be apparent from the following description, the accompanying drawings and the appended claims.

All patents, patent applications and publications mentioned in this specification are herein incorporated by reference to the same extent as if each individual publication or patent application was specifically and individually indicated to be incorporated by reference.

In addition, it is intended that combinations of aspects of the systems and methods described herein as well as the various embodiments themselves, where possible, are within the scope of this disclosure.

DETAILED DESCRIPTION OF THE INVENTION

As used in the specification, "a" or "an" means one or more. As used in the claim(s), when used in conjunction with the word "comprising", the words "a" or "an" mean one or more. As used herein, "another" means as least a second or more. "Substantially" or "substantial" mean largely but not entirely. For example, substantially may mean about 10% to about 99.999, about 25% to about 99.999% or about 50% to about 99.999%.

Treatment Media Source, Energy Source, Controller

Figure 2:
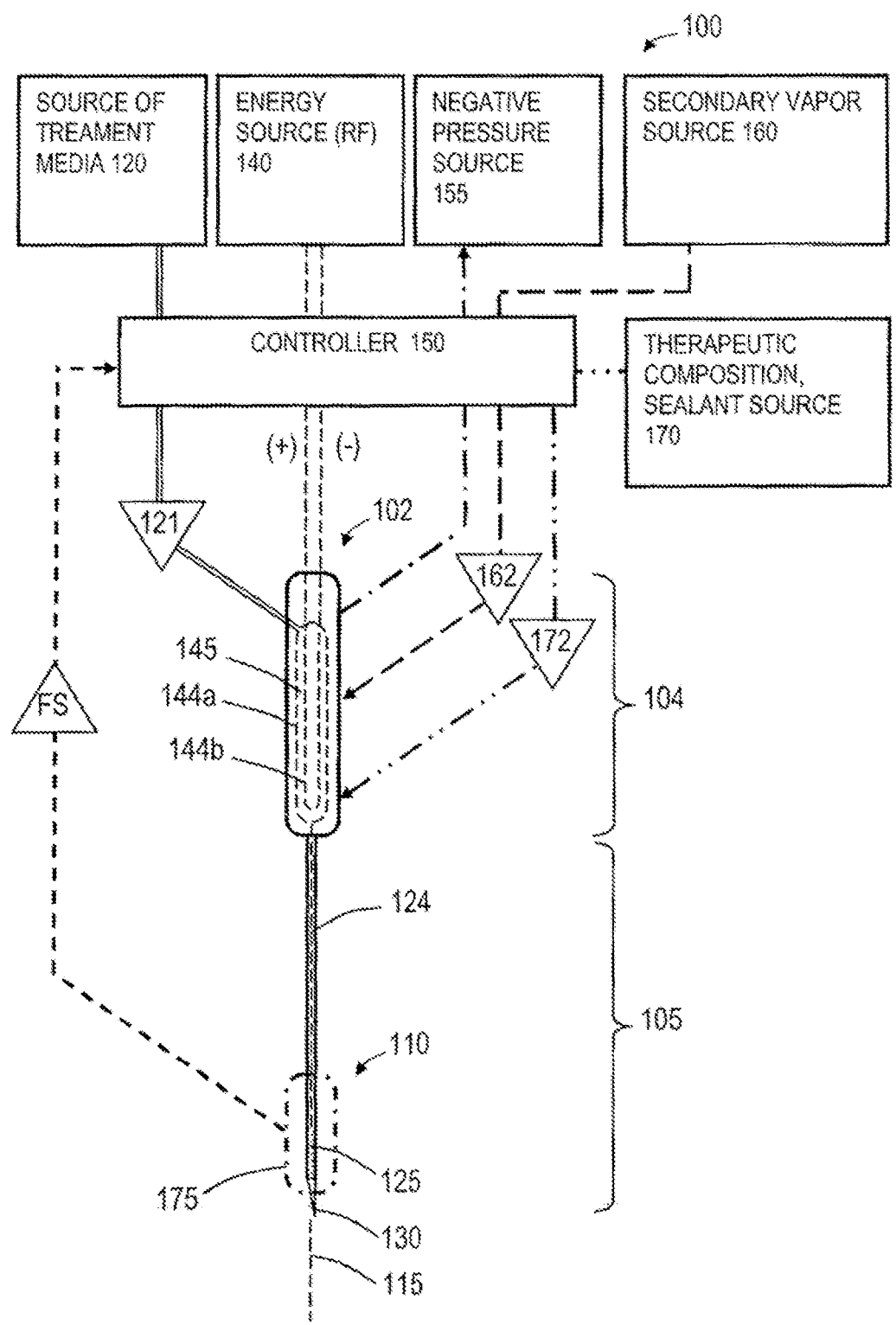
FIG. 2 is a schematic view of medical system that is adapted to treating a target tissue.

Referring to FIG. 2, a schematic view of medical system 100 of the present invention is shown that is adapted for treating a tissue target, wherein the treatment comprises an ablation or thermotherapy and the tissue target can comprise any mammalian soft tissue to be ablated, scaled, contracted, coagulated, damaged or treated to elicit an immune response. The system 100 include an instrument or probe body 102 with a proximal handle end 104 and an extension portion 105 having a distal or working end indicated at 110. In one embodiment depicted in FIG. 2, the handle end 104 and extension portion 105 generally extend about longitudinal axis 115. In the embodiment of FIG. 2, the extension portion 105 is a substantially rigid tubular member with at least one flow channel therein, but the scope of the invention encompasses extension portions 105 of any mean diameter and any axial length, rigid or flexible, suited for treating a particular tissue target. In one embodiment, a rigid extension portion 105 can comprise a 20 Ga. to 40 Ga. needle with a short length for thermal treatment of a patient's cornea or a somewhat longer length for treating a patient's retina. In another embodiment, an elongate extension portion 105 can comprise a single needle or a plurality of needles having suitable lengths for tumor or lesion ablation in a liver, breast, gall bladder, bone and the like. In another embodiment, an elongate extension portion 105 can comprise a flexible catheter for introduction through a body lumen to access at tissue target, with a diameter ranging from about 1 to 10 mm. In another embodiment, the extension portion 105 or working end 110 can be articulatable, deflectable or deformable. The probe handle end 104 can be configured as a hand-held member, or can be configured for coupling to a robotic surgical system. In another embodiment, the working end 110 carries an openable and closeable structure for capturing tissue between first and second tissue-engaging surfaces (not shown), which can comprise actuatable components such as one or more clamps, jaws, loops, snares and the like. The proximal handle end 104 of the probe can carry various actuator mechanisms known in the art for actuating components of the system 100, and/or one or more foot-switches can be used for actuating components of the system.

As can be seen in FIG. 2, the system 100 further includes a source 120 of a flowable liquid treatment media 121 that communicates with a flow channel 124 extending through the probe body 102 to at least one outlet 125 in the working end 110. The outlet 125 can be singular or multiple and have any suitable dimension and orientation as will be described further below. The distal tip 130 of the probe can be sharp for penetrating tissue, or can be blunt-tipped or open-ended with outlet 125.

In one embodiment shown in FIG. 2, an RF energy source 140 is operatively connected to a thermal energy source or emitter (e.g., opposing polarity electrodes 144a, 144b) in interior chamber 145 in the proximal handle end 104 of the probe for converting the liquid treatment media 121 from a liquid phase media to a non-liquid vapor phase media 122 with a heat of vaporization in the range of 60° C. to 200° C., or 80° C. to 120° C. A vaporization system using Rf energy and opposing polarity electrodes is disclosed in co-pending U.S. patent application Ser. No. 11/329,381 which is incorporated herein by reference. Another embodiment of vapor generation system is described in detail below in the Section titled "REMOTE VAPOR GENERATION UNIT AND CONTROL SYSTEMS". In any system embodiment, for example in the system of FIG. 2, a controller 150 is provided that comprises a computer control system configured for controlling the operating parameters of inflows of liquid treatment media source 120 and energy applied to the liquid media by an energy source to cause the liquid-to-vapor conversion. The vapor generation systems described herein can consistently produce a high quality vapor having a temperature of at least 80° C., 100° C. 120° C., 140° C. and 160° C.

As can be seen in FIG. 2, the medical system 100 can further include a negative pressure or aspiration source indicated at 155 that is in fluid communication with a flow channel in probe 102 and working end 110 for aspirating treatment vapor media 122, body fluids, ablation by-products, tissue debris and the like from a targeted treatment site, as will be further described below. In FIG. 2, the controller 150 also is capable of modulating the operating parameters of the negative pressure source 155 to extract vapor media 122 from the treatment site or from the interior of the working end 110 by means of a recirculation channel to control flows of vapor media 122 as will be described further below.

In another embodiment, still referring to FIG. 2, medical system 100 further includes secondary media source 160 for providing an inflow of a second media, for example a biocompatible gas such as $CO_2$. In one method, a second media that includes at least one of depressurized $CO_2$, $N_2$, $O_2$ or $H_2O$ can be introduced and combined with the vapor media 122. This second media 162 is introduced into the flow of non-ionized vapor media for lowering the mass average temperature of the combined flow for treating tissue. In another embodiment, the medical system 100 includes a source 170 of a therapeutic or pharmacological agent or a sealant composition indicated at 172 for providing an additional treatment effect in the target tissue. In FIG. 2, the controller indicated at 150 also is configured to modulate the operating parameters of source 160 and 170 to control inflows of a secondary vapor 162 and therapeutic agents, sealants or other compositions indicated at 172.

In FIG. 2, it is further illustrated that a sensor system 175 is carried within the probe 102 for monitoring a parameter of the vapor media 122 to thereby provide a feedback signal FS to the controller 150 by means of feedback circuitry to thereby allow the controller to modulate the output or operating parameters of treatment media source 120, energy source 140, negative pressure source 155, secondary media source 160 and therapeutic agent source 170. The sensor system 175 is further described below, and in one embodiment comprises a flow sensor to determine flows or the lack of a vapor flow. In another embodiment, the sensor system 175 includes a temperature sensor. In another embodiment, sensor system 175 includes a pressure sensor. In another embodiment, the sensor system 175 includes a sensor arrangement for determining the quality of the vapor media, e.g., in terms or vapor saturation or the like. The sensor systems will be described in more detail below.

Figure 3:
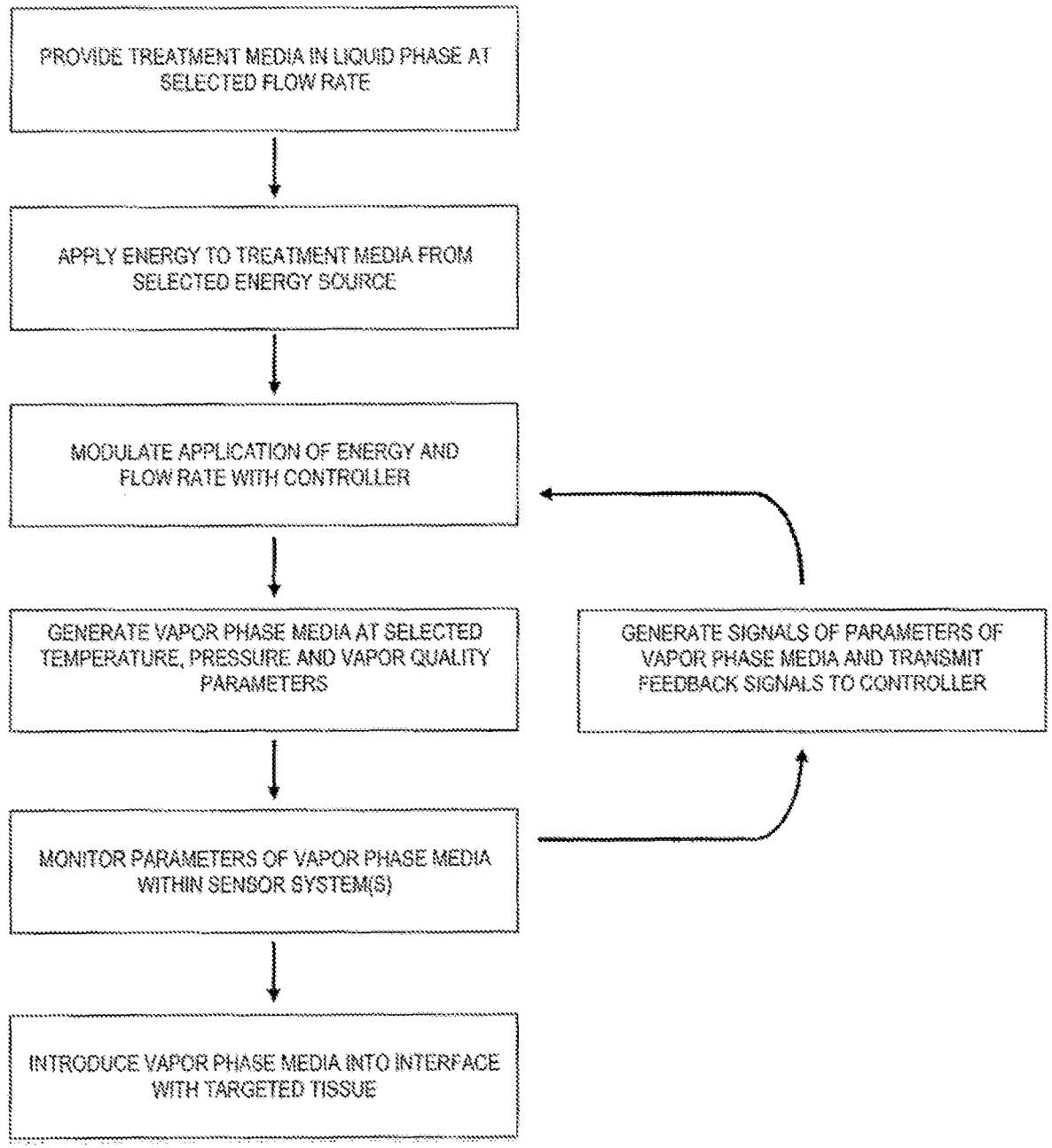
FIG. 3 is a block diagram of a control method of the invention.

Now turning to FIGS. 2 and 3, the controller 150 is capable of all operational parameters of system 100, including modulating the operational parameters in response to preset values or in response to feedback signals FS from sensor system(s) 175 within the system 100 and probe working end 110. In one embodiment, as depicted in the block diagram of FIG. 3, the system 100 and controller 150 are capable of providing or modulating an operational parameter comprising a flow rate of liquid phase treatment media 122 from pressurized source 120, wherein the flow rate is within a range from about 0.001 to 20 ml/min, 0.010 to 10 ml/min or 0.050 to 5 ml/min. The system 100 and controller 150 are further capable of providing or modulating another operational parameter comprising the inflow pressure of liquid phase treatment media 121 in a range from 0.5 to 1000 psi, 5 to 500 psi, or 25 to 200 psi. The system 100 and controller 150 are further capable of providing or modulating another operational parameter comprising a selected level of energy capable of converting the liquid phase media into a non-liquid, non-ionized gas phase media, wherein the energy level is within a range of about 5 to 2,500 watts; 10 to 1,000 watts or 25 to 500 watts. The system 100 and controller 150 are capable of applying the selected level of energy to provide the phase conversion in the treatment media over an interval ranging from 0.1 second to 10 minutes; 0.5 seconds to 5 minutes, and 1 second to 60 seconds. The system 100 and controller 150 are further capable of controlling parameters of the vapor phase media including the flow rate of non-ionized vapor media proximate an outlet 125, the pressure of non-ionized vapor media at the outlet, the temperature or mass average temperature of the vapor media, and the quality of non-ionized vapor media as will be described further below.

Figure 4A:
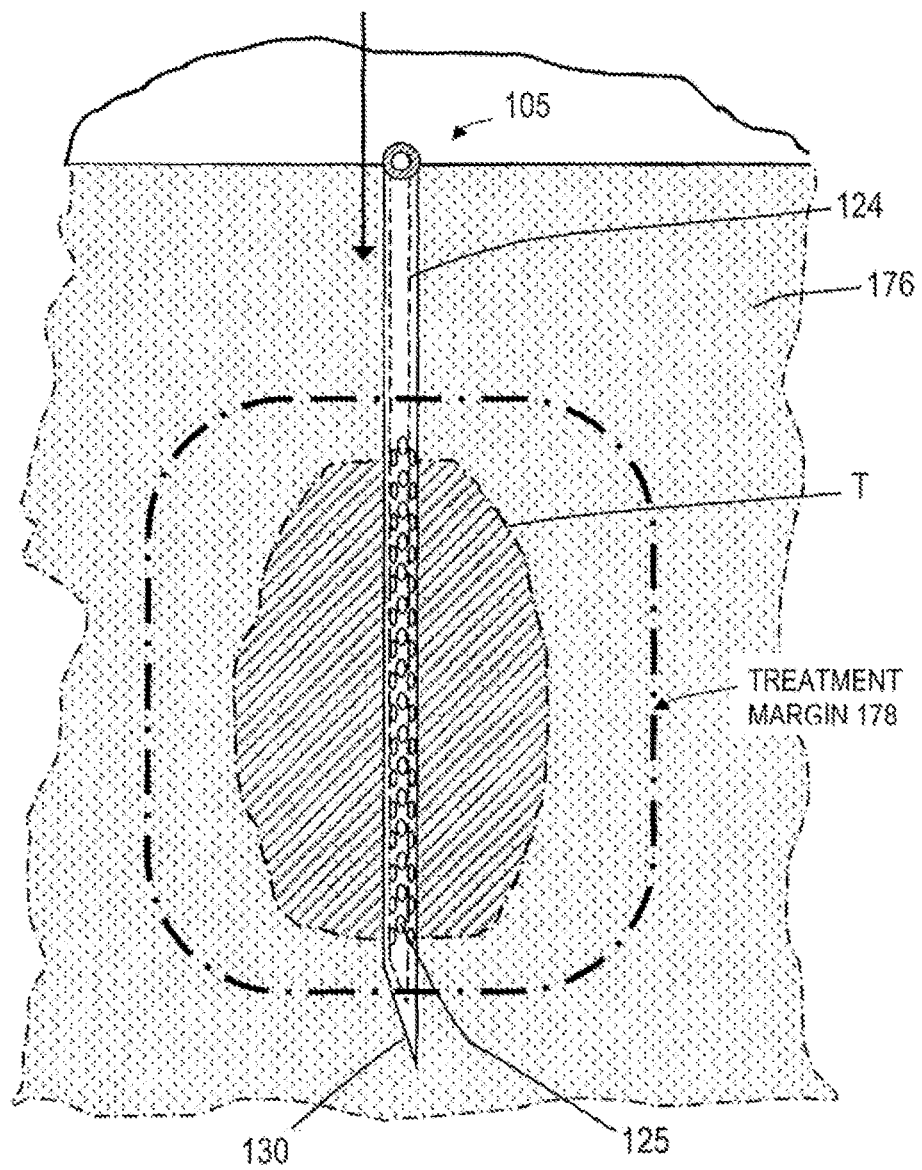
FIG. 4A is an illustration of the working end of FIG. 2 being introduced into soft tissue to treat a targeted tissue volume.
Figure 4B:
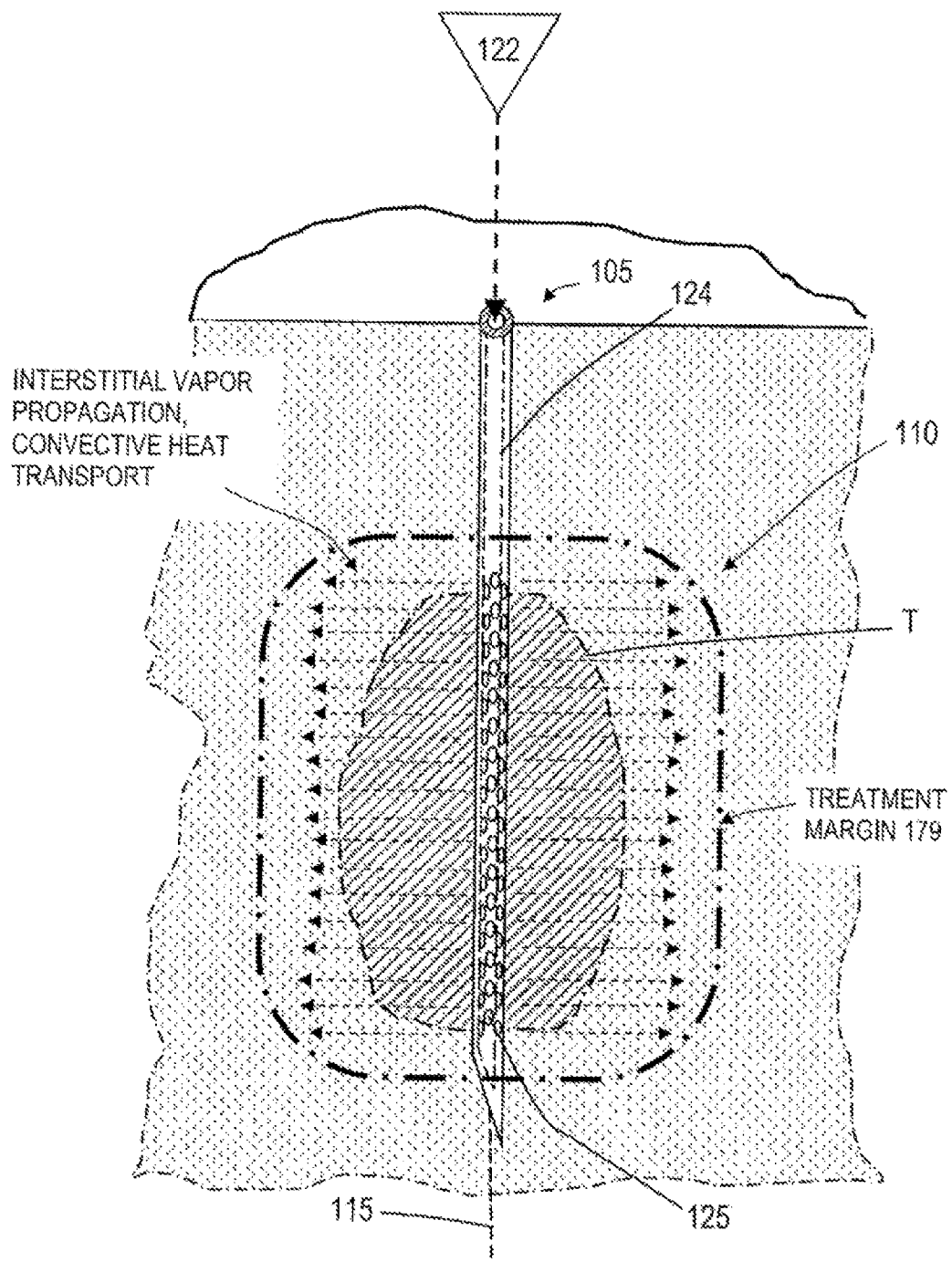
FIG. 4B is an illustration of the working end of FIG. 4A showing the propagation of vapor media in tissue in a method of use in ablating a tumor.

FIGS. 4A and 4B illustrate a working end 110 of the system 100 of FIG. 2 and a method of use. As can be seen in FIG. 4A, a working end 110 is singular and configured as a needle-like device for penetrating into and/or through a targeted tissue T such as a tumor in a tissue volume 176. The tumor can be benign or malignant tissue, for example, in a patient's breast, uterus, lung, liver, kidney, gall bladder, stomach, pancreas, colon, GI tract, bladder, prostate, bone, vertebra, eye, brain or other tissue. In one embodiment of the invention, the extension portion 104 is made of a metal, for example, stainless steel. Alternatively or additionally, at least some portions of the extension portion can be fabricated of a polymer material such as PEEK, PTFE, Nylon or polypropylene. Also optionally, one or more components of the extension portion are formed of coated metal, for example, a coating with Tefloe to reduce friction upon insertion and to prevent tissue sticking following use. In one embodiment at in FIG. 4A, the working end 110 includes a plurality of outlets 125 that allow vapor media to be ejected in all radial directions over a selected treatment length of the working end.

Figure 5:
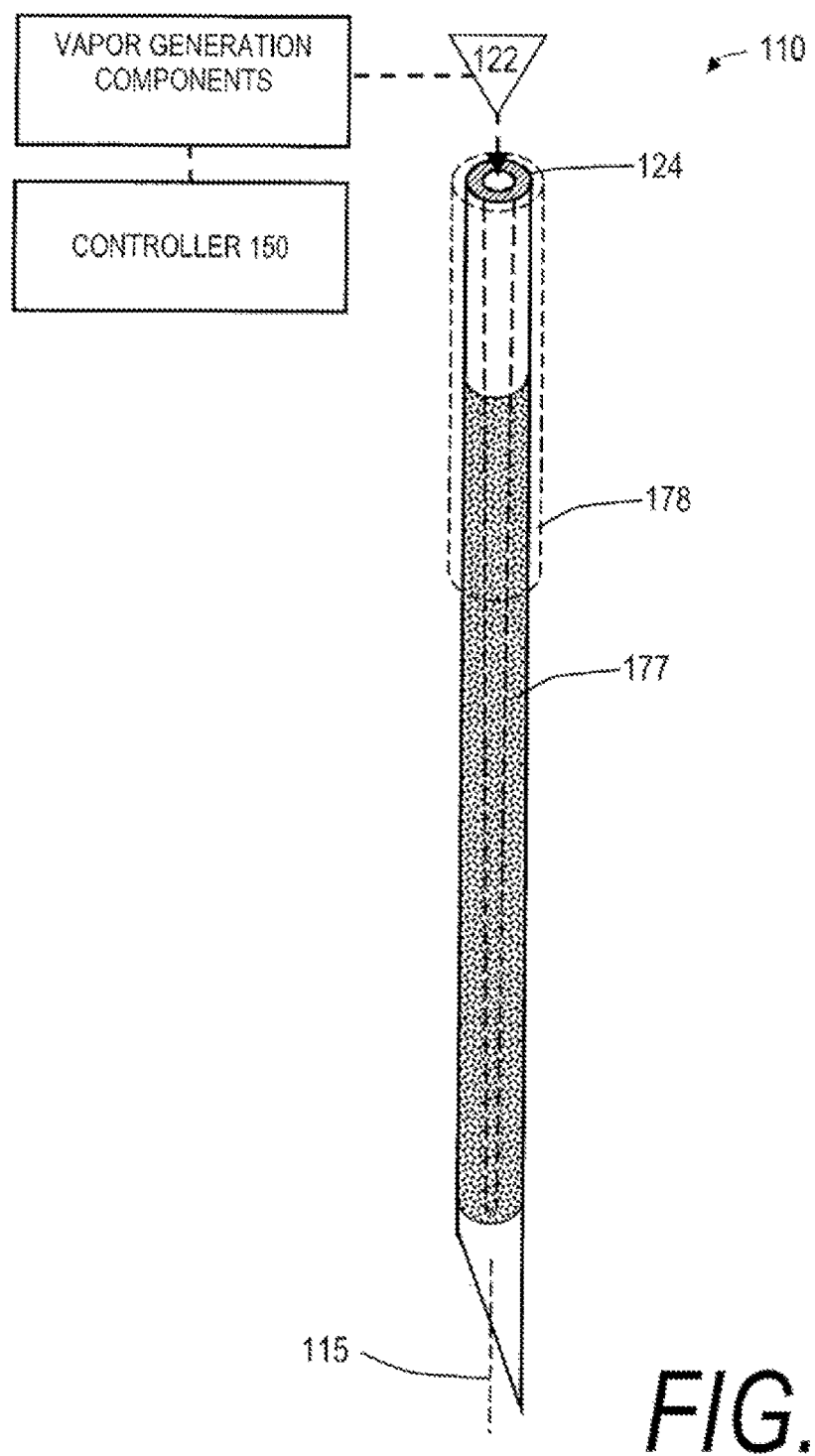
FIG. 5 is an illustration of a working end similar to FIGS. 4A-4B with vapor outlets comprising microporosities in a porous wall.

In one embodiment, the outer diameter of extension portion 105 or working end 110 is, for example, 0.2 mm, 0.5 mm, 1 mm, 2 mm, 5 mm or an intermediate, smaller or larger diameter. Optionally, the outlets can comprise microporosities 177 in a porous material as illustrated in FIG. 5 for diffusion and distribution of vapor media flows about the surface of the working end. In one such embodiment, such porosities provide a greater restriction to vapor media outflows than adjacent targeted tissue which can vary greatly in vapor permeability. In this case, such microporosities ensures that vapor media outflows will occur substantially uniformly over the surface of the working end. Optionally, the wall thickness of the working end 110 is from 0.05 to 0.5 mm. Optionally, the wall thickness decreases or increases towards the distal sharp tip 130 (FIG. 5). In one embodiment, the dimensions and orientations of outlets 125 are selected to diffuse and/or direct vapor media propagation into targeted tissue T and more particularly to direct vapor media into all targeted tissue to cause extracellular vapor propagation and thus convective heating of the target tissue as indicated in FIG. 4B. As shown in FIGS. 4A-4B, the shape of the outlets 125 can vary, for example, round, ellipsoid, rectangular, radially and/or axially symmetric or asymmetric. As shown in FIG. 5, a sleeve 178 can be advanced or retracted relative to the outlets 125 to provide a selected exposure of such outlets to provide vapor injection over a selected length of the working end 110. Optionally, the outlets can be oriented in various ways, for example so that vapor media 122 is ejected perpendicular to a surface of working end 110, or ejected is at an angle relative to the axis 115 or angled relative to a plane perpendicular to the axis. Optionally, the outlets can be disposed on a selected side or within a selected axial portion of working end, wherein rotation or axial movement of the working end will direct vapor propagation and energy delivery in a selected direction. In another embodiment, the working end 110 can be disposed in a secondary outer sleeve that has apertures in a particular side thereof for angular/axial movement in targeted tissue for directing vapor flows into the tissue.

FIG. 4B illustrates the working end 110 of system 100 ejecting vapor media from the working end under selected operating parameters, for example a selected pressure, vapor temperature, vapor quantity, vapor quality and duration of flow. The duration of flow can be a selected pre-set or the hyperechoic aspect of the vapor flow can be imaged by means of ultrasound to allow the termination of vapor flows by observation of the vapor plume relative to targeted tissue T. As depicted schematically in FIG. 4B, the vapor can propagate extracellularly in soft tissue to provide intense convective heating as the vapor collapses into water droplets which results in effective tissue ablation and cell death. As further depicted in FIG. 4B, the tissue is treated to provide an effective treatment margin 179 around a targeted tumorous volume. The vapor delivery step is continuous or can be repeated at a high repetition rate to cause a pulsed form of convective heating and thermal energy delivery to the targeted tissue. The repetition rate vapor flows can vary, for example with flow durations intervals from 0.01 to 20 seconds and intermediate off intervals from 0.01 to 5 seconds or intermediate, larger or smaller intervals.

In an exemplary embodiment as shown in FIGS. 4A-4B, the extension portion 105 can be a unitary member such as a needle. In another embodiment, the extension portion 105 or working end 110 can be a detachable flexible body or rigid body, for example of any type selected by a user with outlet sizes and orientations for a particular procedure with the working end attached by threads or Luer fitting to a more proximal portion of probe 102.

Figure 6A:
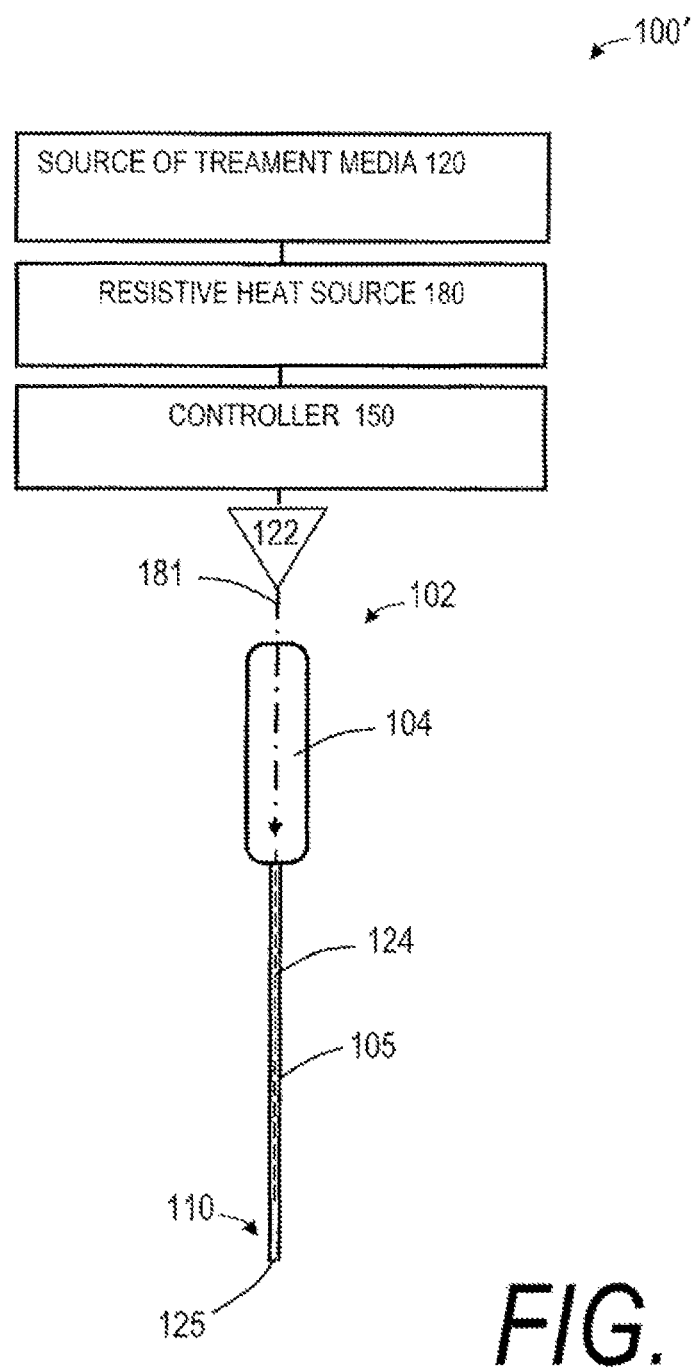
FIG. 6A is another system embodiment with a vapor generator comprising a resistive heating mechanism remote from the probe handle and the needle-like working end.
Figure 6B:
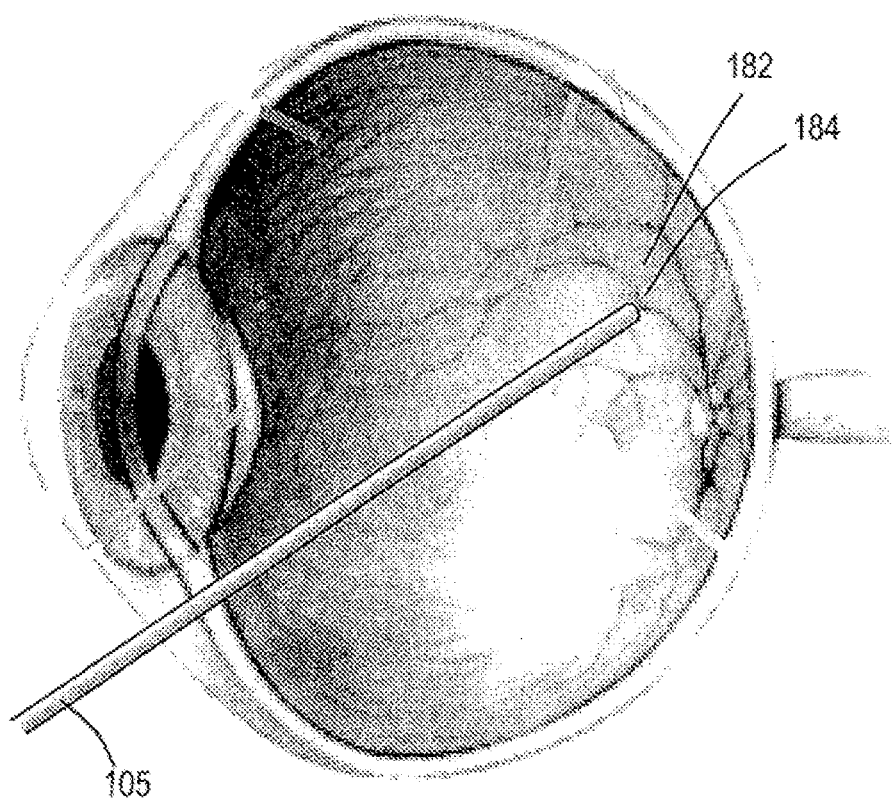
FIG. 6B is an illustration of the working end of FIG. 6A treating retinal tissue.

FIG. 6A illustrates another similar medical system 100' wherein the source 120 of a flowabic liquid treatment media communicates with an energy source 180 comprising a resistive heating system that can be a modular unit and can be remote from the proximal handle end 104 of probe body 102, or the resistive can be within the handle portion or within the extension member 105, or a combination of locations. Thus in one embodiment, the conversion of a liquid media 121 to a vapor media 122 can be accomplished by a resistive heating system and the vapor media can flow through an insulated conduit 181 to communicate with flow channel 124 and then exit the probe 102 at an outlet 125 in the working end 110. The controller 150 again is operatively coupled to all the system sources, sensors and component to control all operational parameters for treating a tissue target. As depicted in FIG. 6B, one embodiment comprised a probe with extension member 105 that comprises a needle member with a blunt or sharp tip for penetration through the sclera or cornea to treat retinal tissue 182, for example to ablate and coagulate blood vessels 184 in a treatment of certain types of macular degeneration. The method can be accompanied by a penetrating endoscope or a slit lamp can be used to localize the treatment.

Sensor Systems for Flows, Temperature, Pressure, Quality

Figure 7:
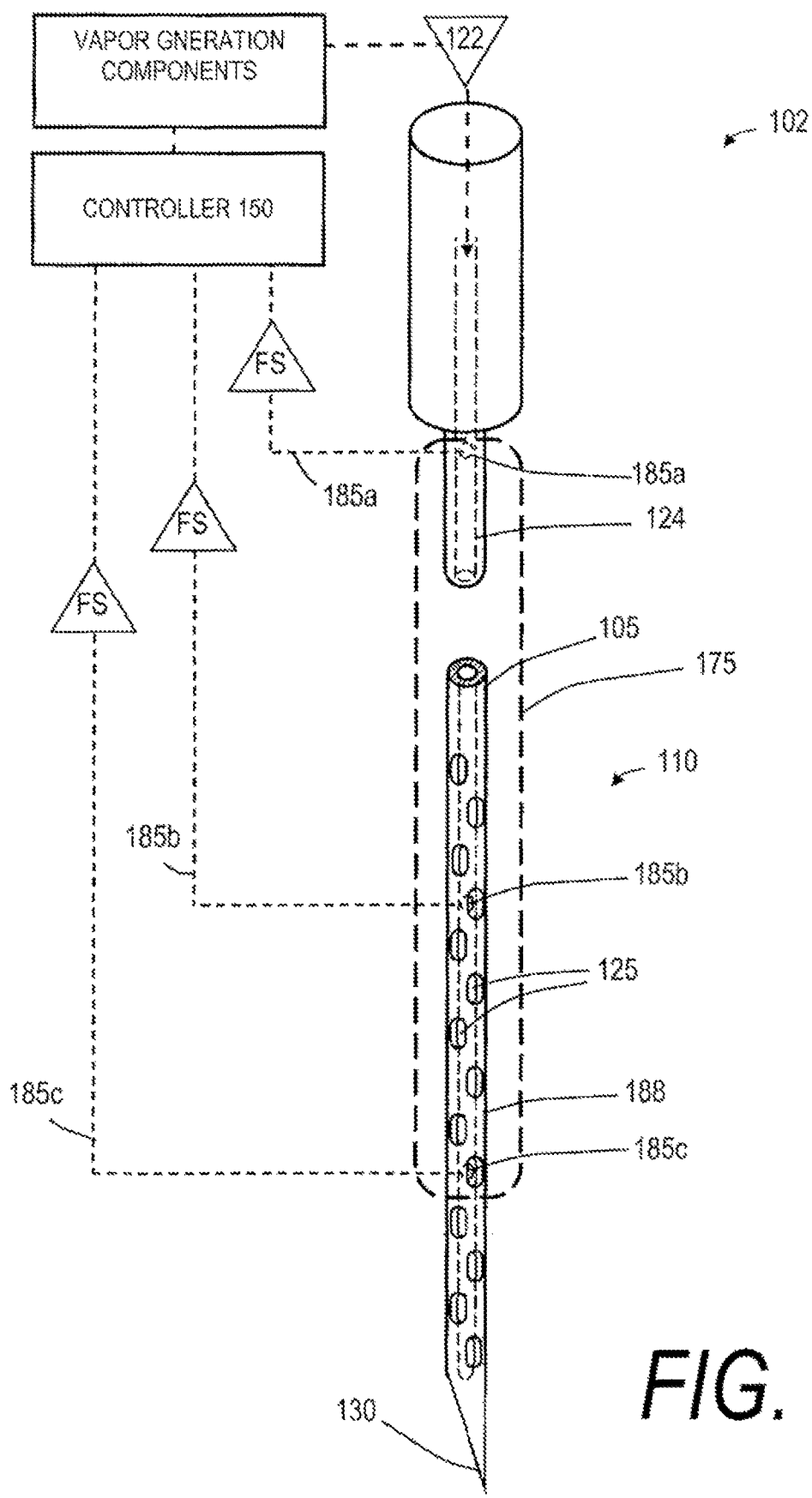
FIG. 7 is an illustration of the needle-like working end as in FIGS. 2 and 4A with a sensor system.

Referring to FIG. 7, one embodiment of sensor system 175 is shown that is carried by working end 110 of the probe 102 depicted in FIG. 2 for determining a first vapor media flow parameter, which can consist of determining whether the vapor flow is in an "on" or "off" operating mode. The working end 110 of FIG. 7 comprises a sharp-tipped needle suited for needle ablation of any neoplasia or tumor tissue, such as a benign or malignant tumor as described previously, but can also be any other form of vapor delivery tool. The needle can be any suitable gauge and in one embodiment has a plurality of vapor outlets 125. In a typical treatment of targeted tissue, it is important to provide a sensor and feedback signal indicating whether there is a flow, or leakage, of vapor media 122 following treatment or in advance of treatment when the system is in "off" mode. Similarly, it is important to provide a feedback signal indicating a flow of vapor media 122 when the system is in "on" mode. In the embodiment of FIG. 7, the sensor comprises at least one thermocouple or other temperature sensor indicated at 185a, 185b and 185c that are coupled to leads (indicated schematically at 186a, 186b and 186c) for sending feedback signals to controller 150. The temperature sensor can be a singular component or can be a plurality of components spaced apart over any selected portion of the probe and working end. In one embodiment, a feedback signal of any selected temperature from any thermocouple in the range of the heat of vaporization of treatment media 122 would indicate that flow of vapor media, or the lack of such a signal would indicate the lack of a flow of vapor media. The sensors can be spaced apart by at least 0.1 mm, 0.5 mm, 1 mm, 5 mm, 10 mm and 50 mm. In other embodiments, multiple temperature sensing event can be averaged over time, averaged between spaced apart sensors, the rate of change of temperatures can be measured and the like. In one embodiment, the leads 186a, 186b and 186c are carried in an insulative layer of wall 188 of the extension member 105. The insulative layer of wall 188 can include any suitable polymer or ceramic for providing thermal insulation. In one embodiment, the exterior of the working end also is also provided with a lubricious material such as Teflon® which further insures against any tissue sticking to the working end 110.

Still referring to FIG. 7, a sensor system 175 can provide a different type of feedback signal FS to indicate a flow rate or vapor media based on a plurality of temperature sensors spaced apart within flow channel 124. In one embodiment, the controller 150 includes algorithms capable of receiving feedback signals FS from at least first and second thermocouples (e.g., 185a and 185c) at very high data acquisition speeds and compare the difference in temperatures at the spaced apart locations. The measured temperature difference, when further combined with the time interval following the initiation of vapor media flows, can be compared against a library to thereby indicate the flow rate.

Figure 8:
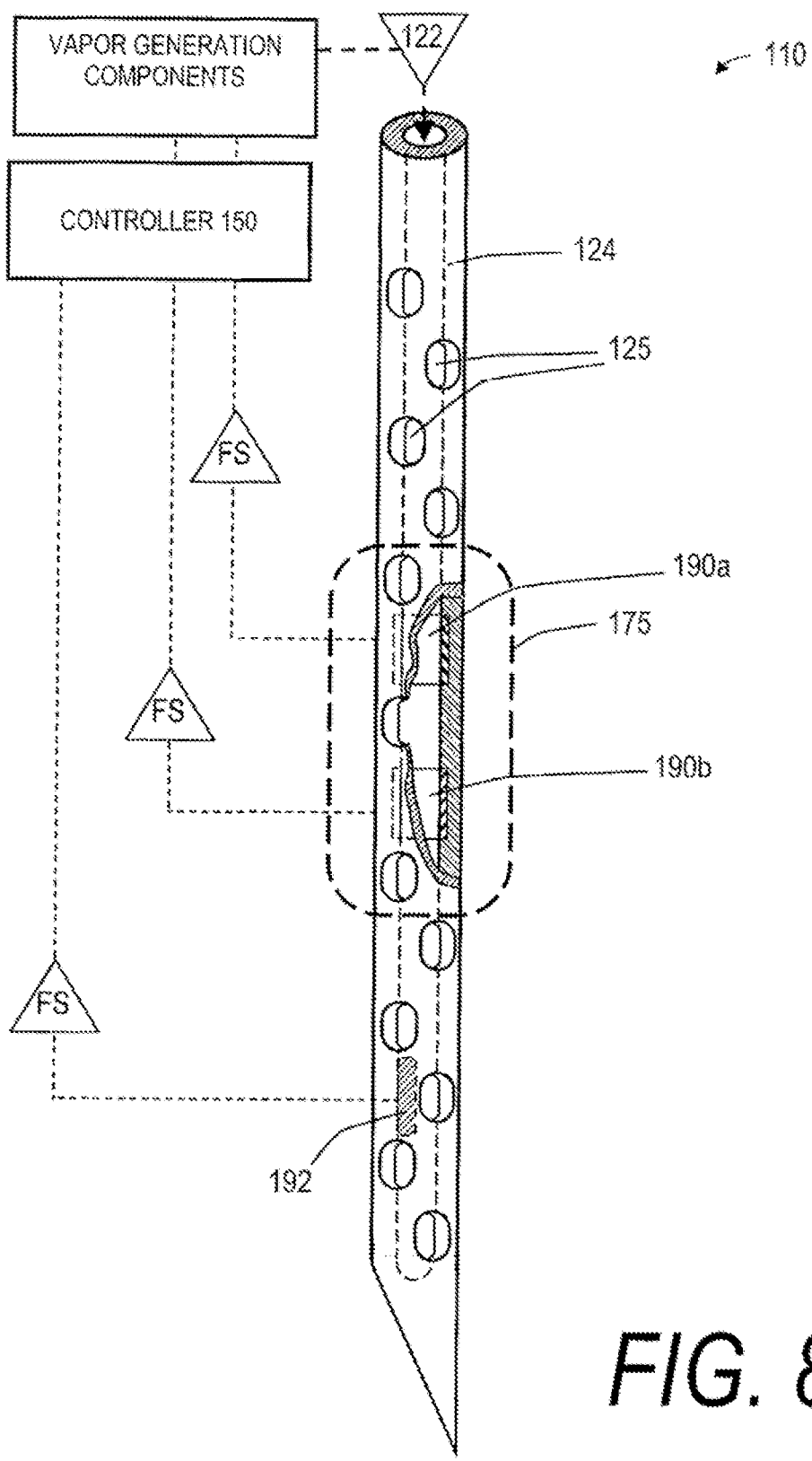
FIG. 8 is an illustration of a working end including an expandable member.

Another embodiment of sensor system 175 in a similar working end 110 is depicted in FIG. 8, wherein the sensor is configured for indicating vapor quality—in this case based on a plurality of spaced apart electrodes 190a and 190b coupled to controller 150 and an electrical source (not shown). In this embodiment, a current flow is provided within a circuit to the spaced apart electrodes 190a and 190b and during vapor flows within channel 124 the impedance will vary depending on the vapor quality or saturation, which can be processed by algorithms in controller 150 and can be compared to a library of impedance levels, flow rates and the like to thereby determine vapor quality. It is important to have a sensor to provide feedback of vapor quality which determines how much energy is being carried by a vapor flow. The term "vapor quality" is herein used to describe the percentage of the flow that is actually water vapor as opposed to water droplets that is not phase-changed. In another embodiment (not shown) an optical sensor can be used to determine vapor quality wherein a light emitter and receiver can determine vapor quality based on transmissibility or reflectance of a vapor flow.

Figure 1A:
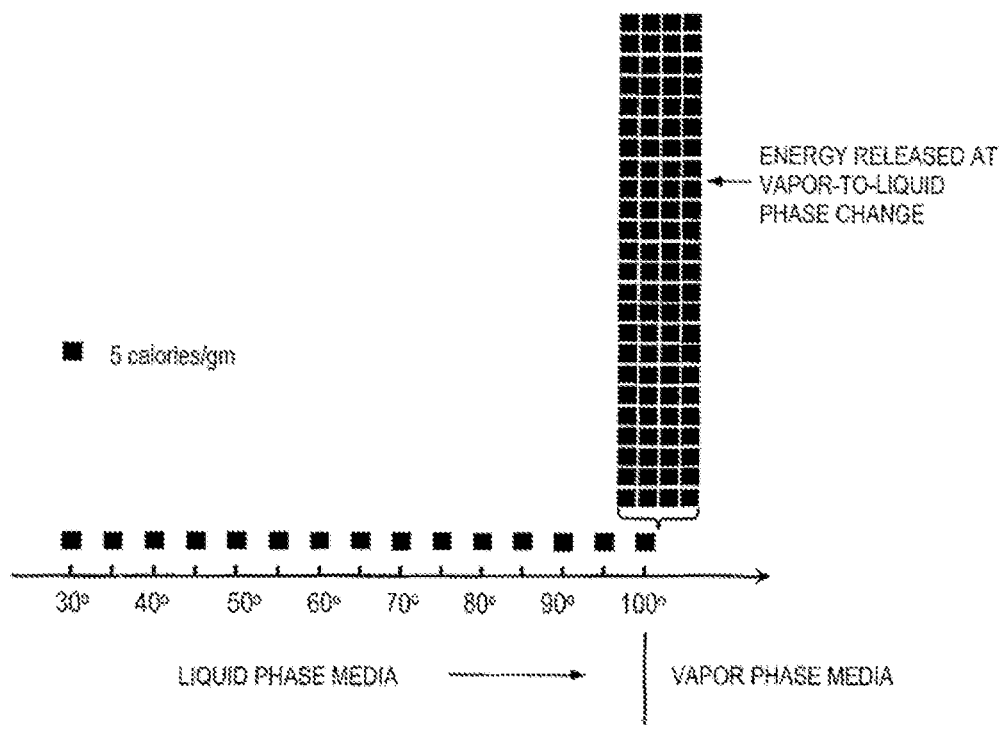
FIG. 1A is a graphical depiction of the quantity of energy needed to achieve the heat of vaporization of water.
Figure 1B:
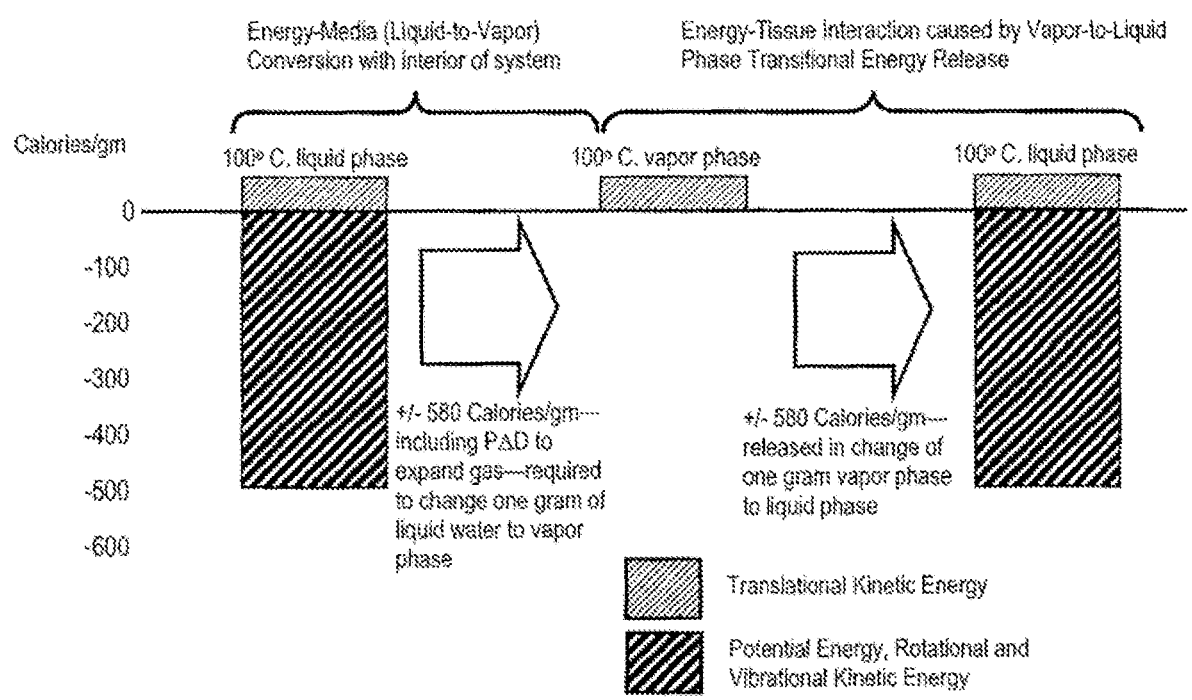
FIG. 1B is a diagram of phase change energy release that underlies a system and method of the invention.

FIG. 8 further depicts a pressure sensor 192 in the working end 110 for providing a signal as to vapor pressure. In operation, the controller can receive the feedback signals FS relating to temperature, pressure and vapor quality to thereby modulate all other operating parameters described above to optimize flow parameters for a particular treatment of a target tissue, as depicted in FIG. 1. In one embodiment, a MEMS pressure transducer is used, which are known in the art. In another embodiment, a MEMS accelerometer coupled to a slightly translatable coating can be utilized to generate a signal of changes in flow rate, or a MEMS microphone can be used to compare against a library of acoustic vibrations to generate a signal of flow rates.

Figure 9A:
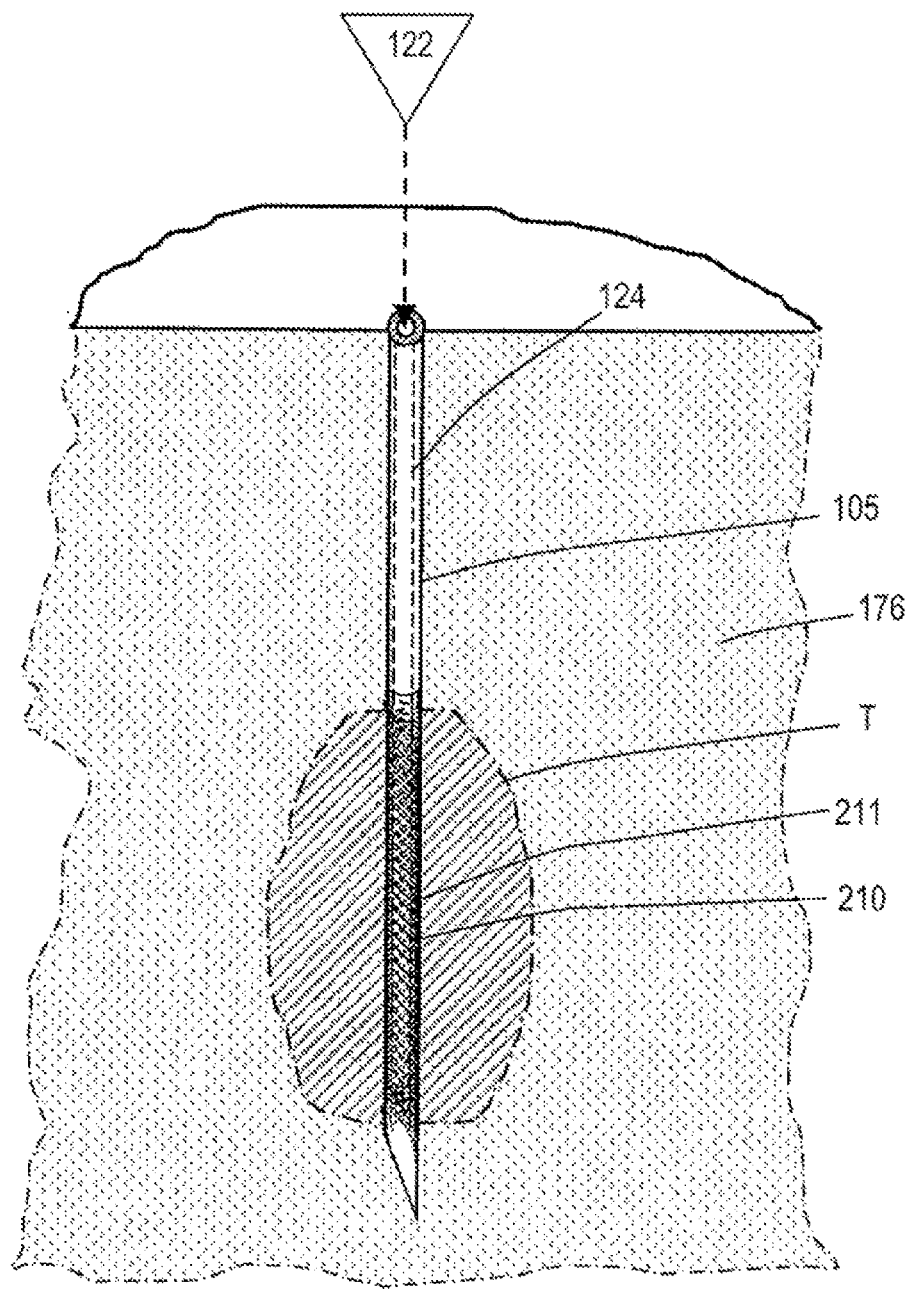
FIG. 9A is an illustration of an expandable working end being introduced into soft tissue.
Figure 9B:
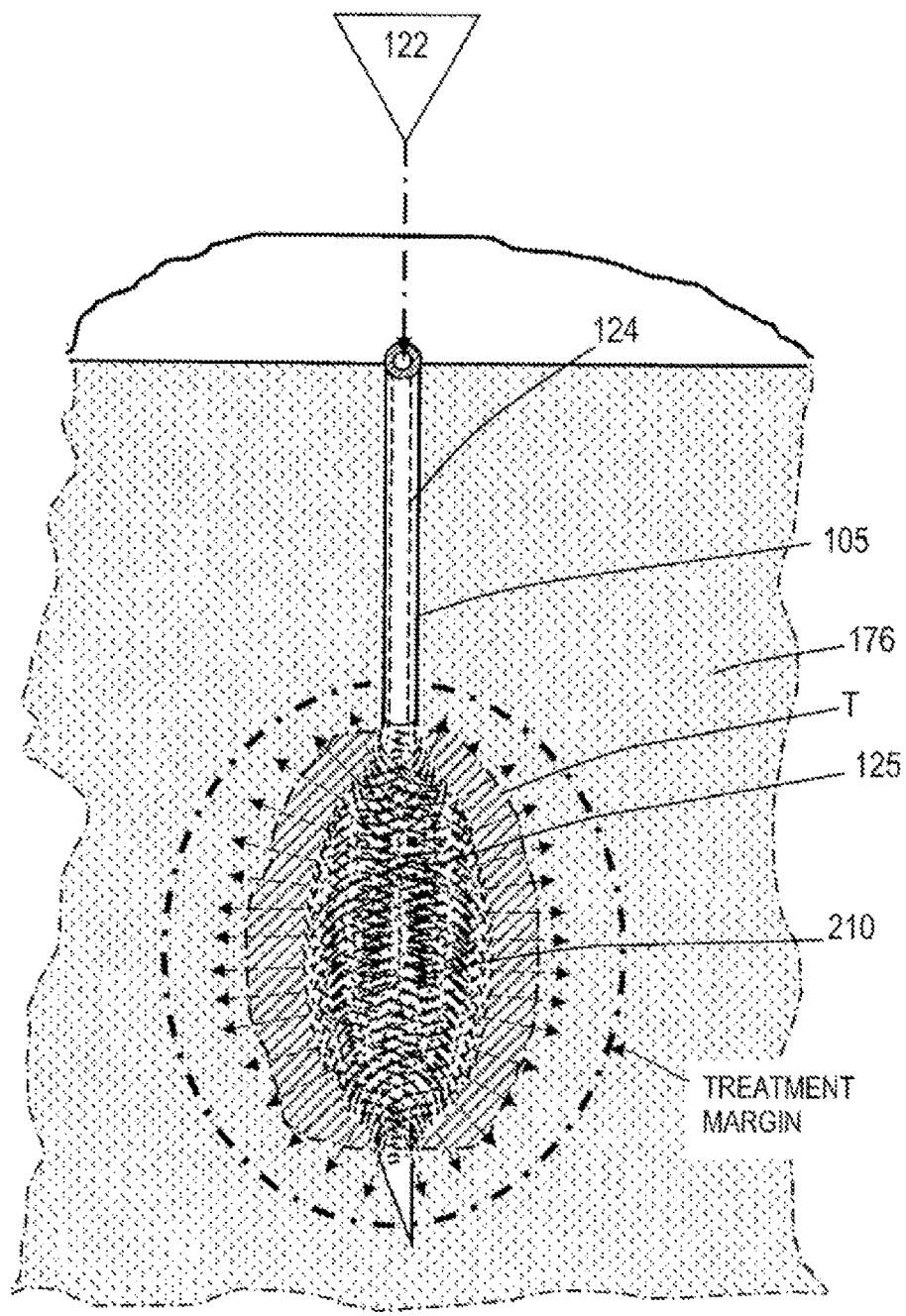
FIG. 9B is an illustration of the working end of FIG. 9A showing the propagation of vapor media in tissue to ablate tumorous tissue.

FIGS. 9A and 9B illustrate another embodiment of vapor delivery tool and working end 110 that is coupled to a vapor source and controller 150 as described above (see FIG. 2). In this embodiment, the extension member 105 is similar to that of FIGS. 4A and 4B but includes an expandable working end indicated at 210. As can be seen in FIGS. 9A-9B, the working end includes a region that is woven, knit or braided from wire-like metal or polymer filaments 211 around a flow channel 124 that extends through extension member 105 and wherein the inflow pressure of the vapor 122 is controlled to cause expansion of the woven filament working end at the same time as diffusing the vapor flow from the plurality of outlets 125 can between the filaments 211 (FIG. 9B). The expansion of the working end is adapted to apply compression against the soft tissue and tumor T to thereby alter convective heating effects in such tissue. Such compression increases local tissue density and can make tissue density more uniform, for example, by collapsing vessel and lumens in the targeted tissue which may otherwise cause a pathway for convective heat transfer to migrate non-uniformly.

Figure 10A:
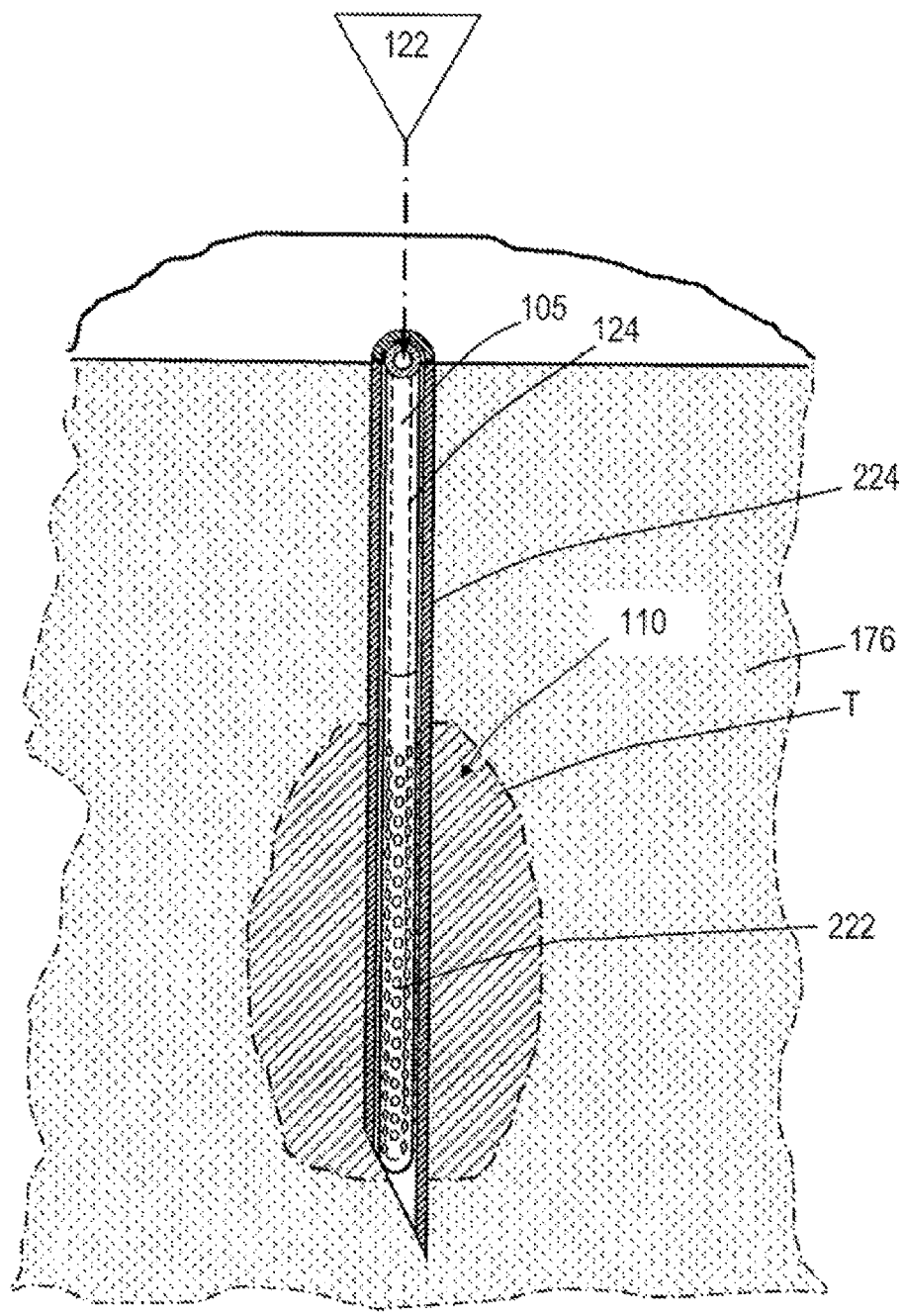
FIG. 10A is an illustration of an expandable working end and sleeve being introduced into soft tissue.
Figure 10B:
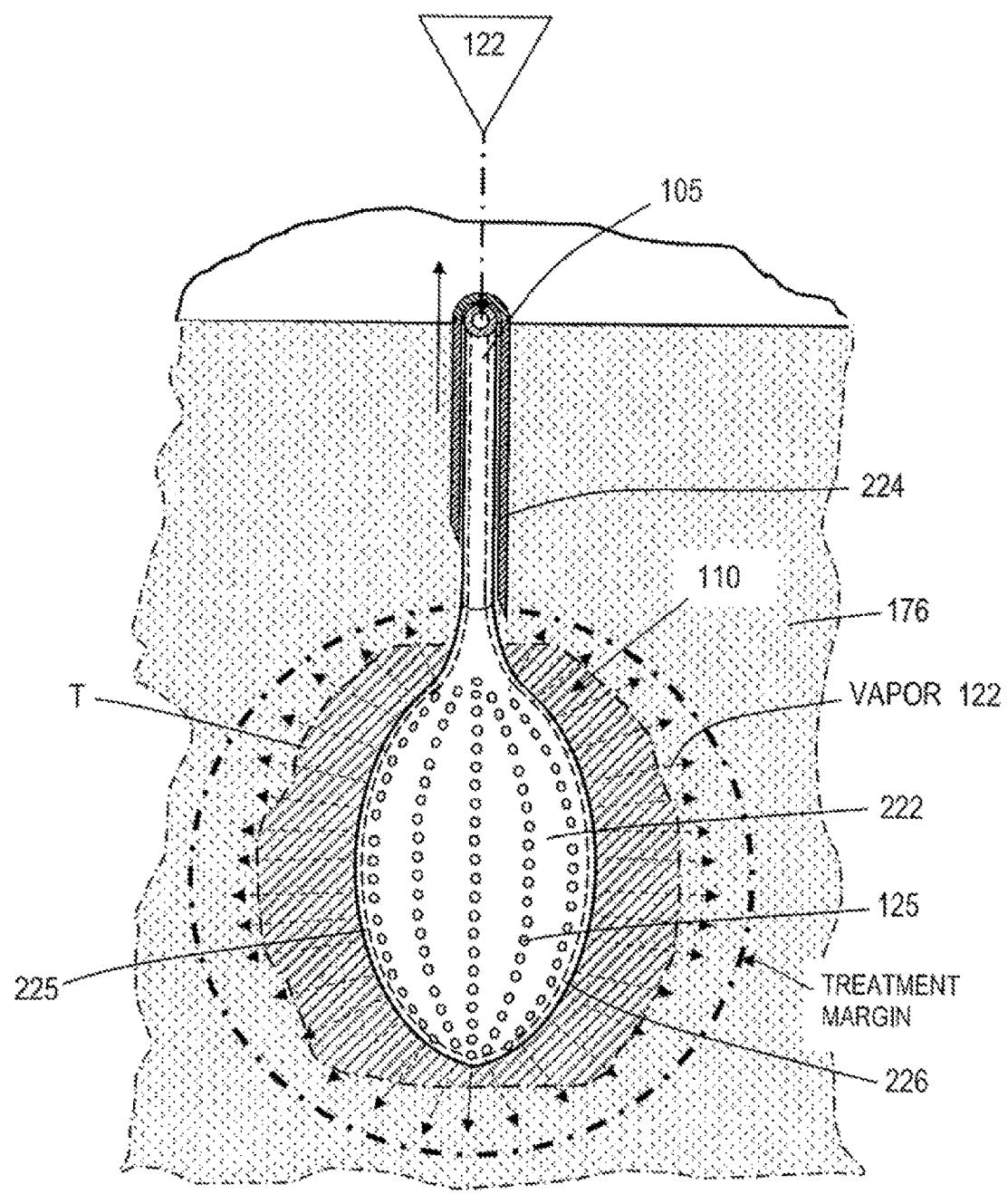
FIG. 10B is an illustration of the working end of FIG. 10A showing the propagation of vapor media in tissue.

FIGS. 10A and 10B illustrate another vapor delivery tool with an extension member 105 having a working end 110 that carries a non-complaint or compliant expandable structure 222 such as a balloon made of any suitable temperature resistant polymer known in the art. The balloon 222 can be sealed and coupled to the extension member 105 by adhesives or collars. In a method of use as shown in FIGS. 10A-10B, the expandable working end 220 can be carried is a retractable sheath 224 that is inserted into tissue (FIG. 10A) and then withdrawn to dispose the working end 110 in the targeted tissue. The balloon 222 has an interior chamber 225 with a wall 226 that is microporous or has plurality of outlets 125 therein as depicted in FIG. 10B. As can be seen in FIG. 10B, the inflow of vapor 122 from source 120 is modulated by a controller 150 to expand the balloon 222. Thereafter, the vapor propagates from the outlets 125 in the balloon wall to apply energy to the tissue interfacing with the balloon wall.

Figure 11:
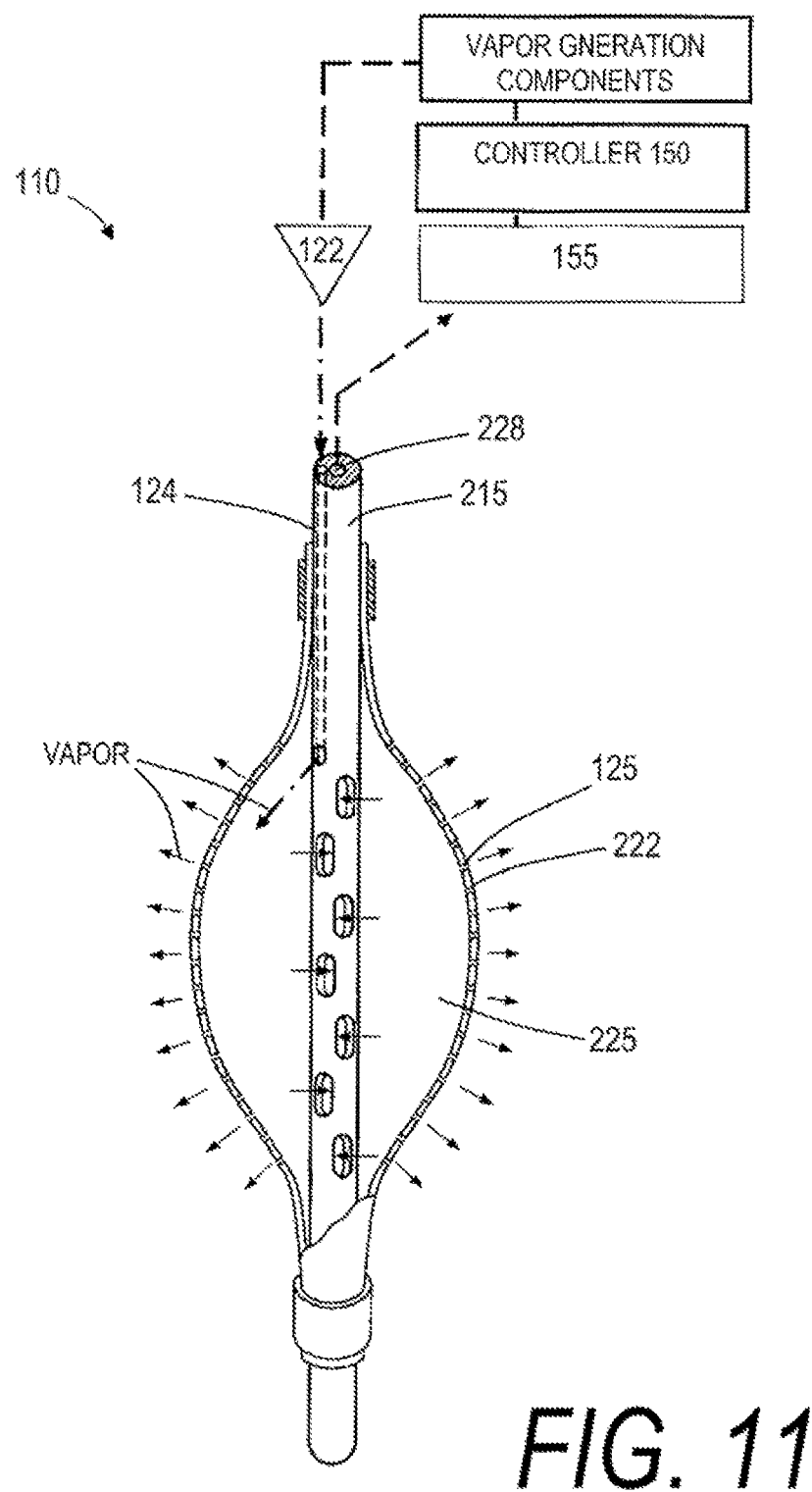
FIG. 11 is a cut-away view of a expandable working end with a recirculation flow channel.

FIG. 11 is a cutaway view of another vapor delivery tool or probe with extension member 105 and working end 110 that includes an expandable structure 222 similar to that of FIGS. 10A-10B. The embodiment of FIG. 11 includes a first flow channel 124 for carrying the vapor into the interior chamber 225 of the expandable structure 222 and a second recirculating flow channel 228 in communication with negative pressure source 155 for aspiration or extraction of a flow of media from the interior chamber 225. This embodiment thus uses both a pressurized inflow source 120 and the recirculation channel 228 coupled to negative pressure source 155 to allow the controller to precisely modulate flow from outlets 125 in the expandable structure 222. The embodiment of FIG. 11 is shown for convenience with a substantially symmetrical balloon, but it should be appreciated that the balloon can be any symmetric, elongated, complex or asymmetric shape and can be configured for deployment and expansion in soft tissue or can be configured for deployment in a body cavity or lumen, such as a blood vessel, AVM, a patient's uterus, a nasal passageway or sinus, a gall bladder or other hollow organ, the gastrointestinal tract or the respiratory tract. The expandable structure 222 or balloon can have multiple chambers with internal constraining elements to allow the balloon to deployably expand to an asymmetric shape.

Figure 12A:
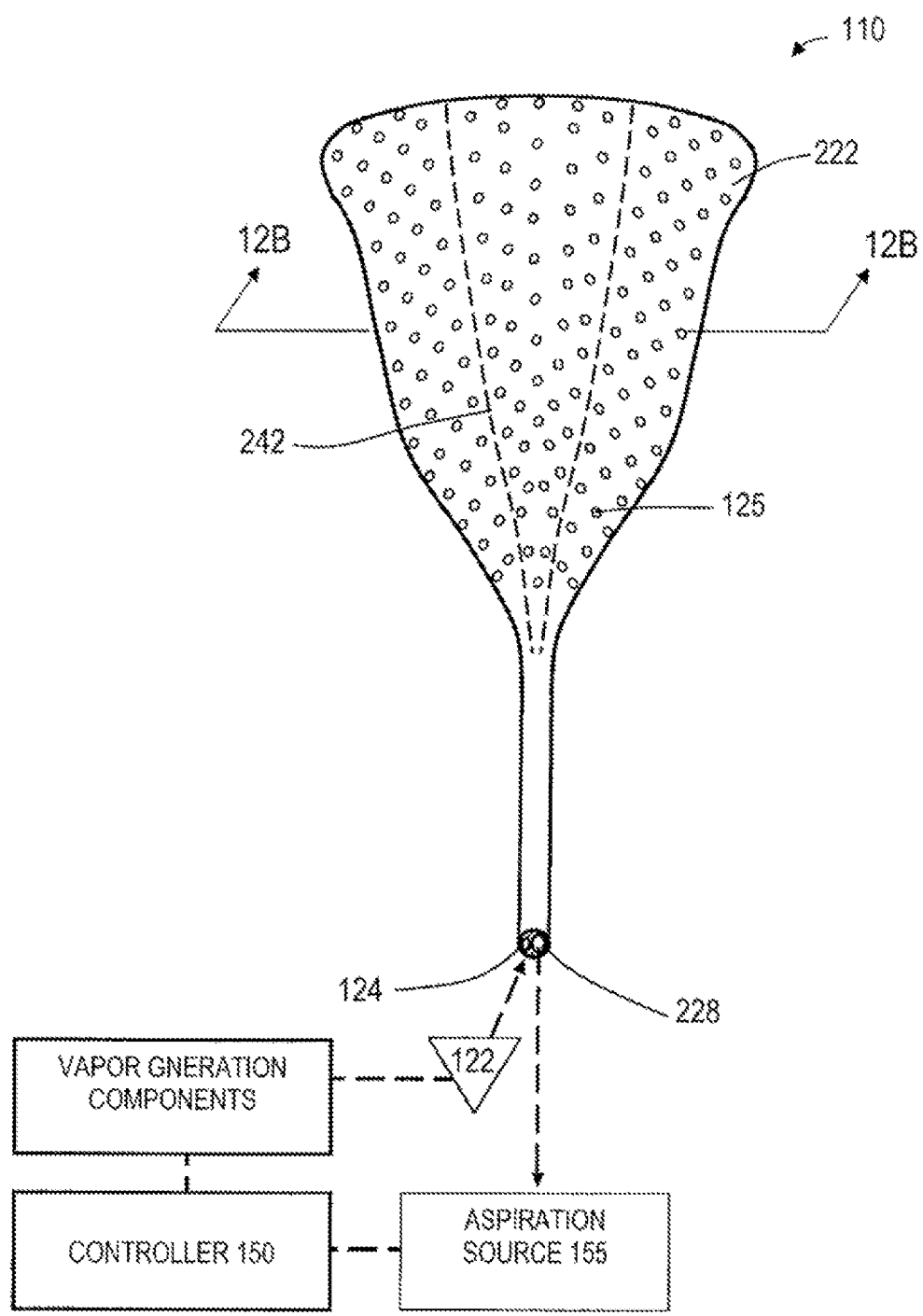
FIG. 12A is an illustration of an expandable working end configured for positioning in a uterine cavity for an endometrial ablation treatment.
Figure 12B:
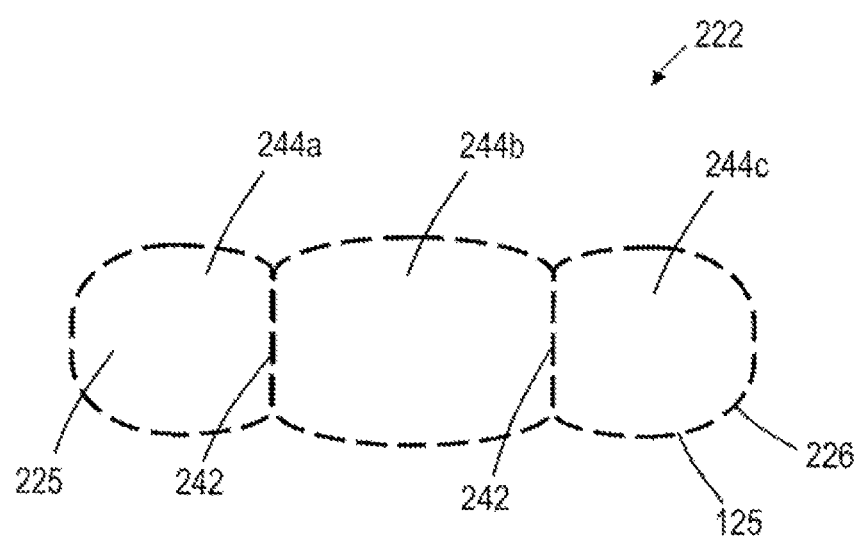
FIG. 12B is a sectional view of the expandable working end of FIG. 12A.

FIGS. 12A and 12B depict another system and working end 110 with an asymmetric shaped expandable structure 222 configured for deployment in a patient's uterus to apply energy for an endometrial ablation treatment. It can be seen that expandable structure 222 is shaped to occupy the cavity of a uterus and has a plurality of interior chamber portions 225 collectively in FIG. 12B separated by a vapor impermeable or permeable wall 242. The expandable structure 222 can have from 2 to 100 or more such chambers and is shown in FIGS. 12A and 12B with three chamber portions 244a, 244b, 244c. The balloon wall 226 has vapor outlets 125 as described previously, and further includes the recirculation channel 228 and pressure control system as described in the embodiment of FIG. 11. The expandable structure 222 of FIG. 12B is shown with a plurality of outlets 125 or porosities in the wall 226 of the balloon, and it should be appreciated that the outlets can vary in density and dimension to permit greater and lesser vapor propagation through selected regions of the wall. For example, greater vapor flows can be directed to thicker endometrial portions to increase the depth of ablation, and lesser vapor flows can be directed to thinner layers of the endometrium and toward the fallopian tubes.

Figure 12C:
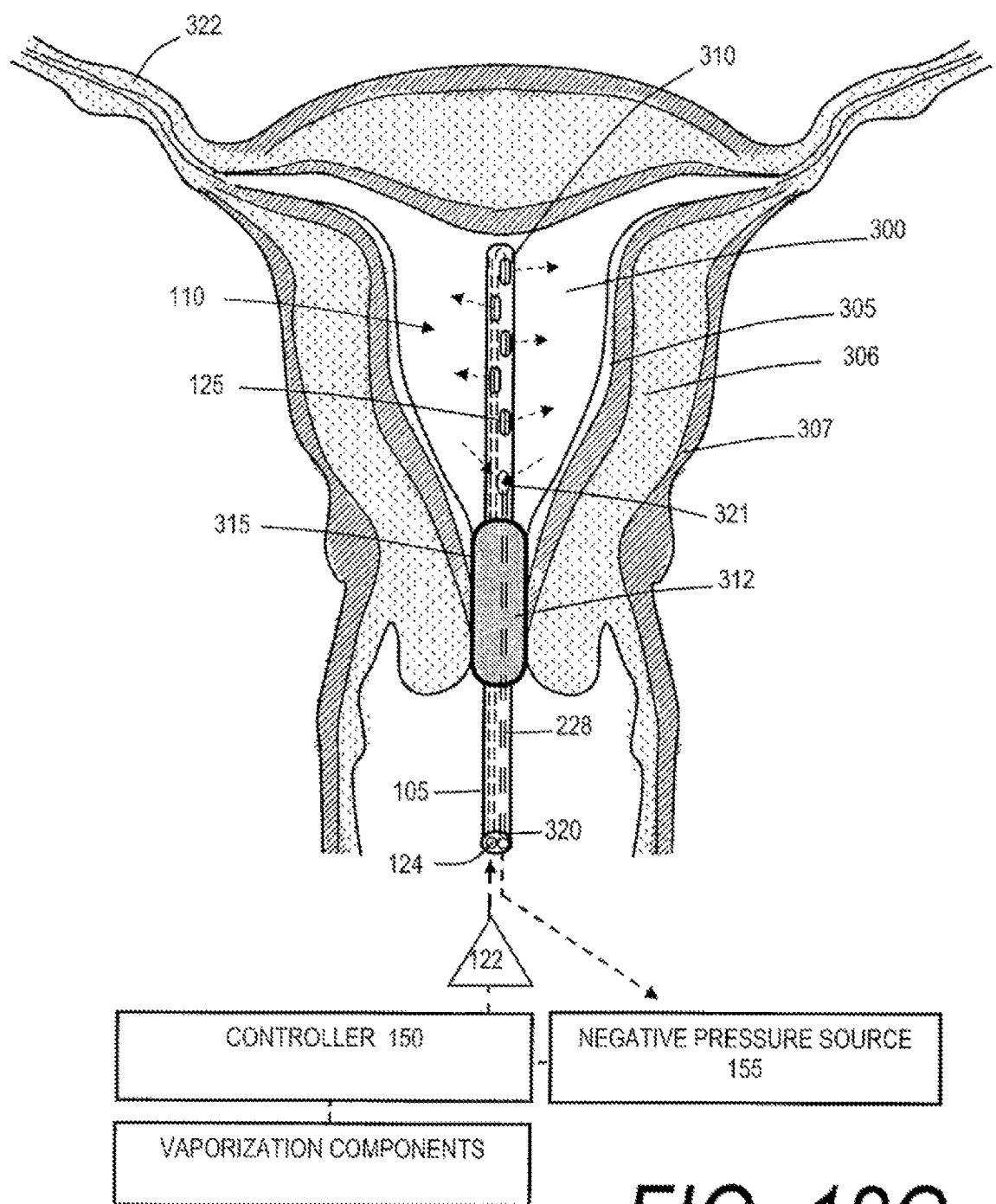
FIG. 12C is a view of another non-expandable working end in an endometrial ablation treatment method.

FIG. 12C illustrates another probe embodiment for applying energy to a body cavity and more particularly to a uterine cavity 300 for accomplishing an endometrial ablation treatment. This embodiment is similar to that of FIGS. 4A-4B wherein the working end 110 is a non-expandable tubular member. FIG. 12C illustrates the endometrium 305 that is targeted for ablation to treat menorrhagia. The endometrium 305 is the uterine lining that is inward of the myometrium 306 and perimetrium 307. The embodiment of FIG. 12C has working end 110 that has a soft or blunt distal tip 310 that is dimensioned for insertion through cervix 312. The working end 110 can range from about 2 mm to 8 mm in diameter, and can have a vapor delivery lumen 124 that is substantially small for vapor delivery to one or more outlets 125 with the outlets distal of expandable balloon 315. The extension member 105 includes with a substantial insulative layer 320 (further described below) that extends to the working end 110. In this embodiment, the extension member 105 and working end 110 can be fabricated of a polymer material such as PEEK, PTFE, Nylon or polypropylene and a plurality of outlets 125 for vapor ejection can be provided in selected radial directions over a selected length of the working end 110. In another embodiment, the working end 110 can have a single outlet 125. In one embodiment, the working end 110 has an expansion member or balloon 315 positioned proximal to the vapor outlet(s) 125 to prevent proximal vapor flows retrograde from the uterine cavity and to protect the cervix 312 from high temperatures. The deployment of balloon 315 can further allow a selected pressure to be maintained in the cavity wherein another lumen 228 (aspiration lumen) with port 321 in the working end is coupled to negative pressure source 155 that includes a valve configured to control outflows from the uterine cavity with the valve operatively connected to controller 150. In another embodiment, the working end 110 can include any inflatable, actuatable or spring-like frame to distend the cavity in the uterus, as well as expandable balloons or similar structures (not shown) for preventing vapor flow into the fallopian tubes 322. As can be understood from FIG. 12C, the endometrial ablation system can have all of the features, sensors and subsystems described elsewhere herein in the various embodiments. In one method, the system and controller can utilize the controller 150 and valve connected to the aspiration lumen 228 in the probe valve to provide a pressure in the uterus during treatment ranging between 0.1 psi and 50 psi, between 0.2 psi and 10 psi, and between 0.5 psi and 5 psi. In the embodiment of FIG. 12C, the inflation lumen to expand the balloon 322 is not shown and can be manually operated or can be operatively coupled to controller 150. In another method, the system allows controlled distension of a body cavity with a gas or vapor media, such as a uterine cavity, in combination with the vapor media applying a selected amount of ablative energy uniformly about the surface of the distended body cavity.

Figure 12D:
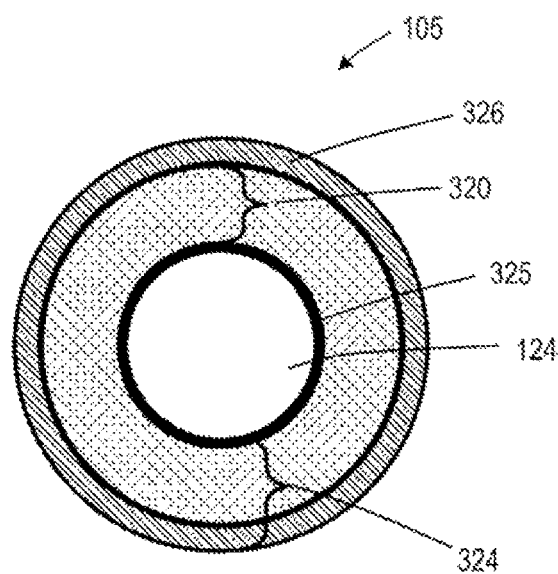
FIG. 12D is a view of a cross-section of an insulative wall portion of a vapor delivery probe.

In another aspect of the invention, a vapor delivery system as described above can have an extension member 105 (FIGS. 4A-12C) with an insulative wall, as depicted in the cross-sectional view of FIG. 12D. In FIG. 12D, it can be seen that at least one flow channel 124 is within an interior of the surrounding structure or wall 324 that includes a thermally insulative layer or region indicated at 320. In one embodiment, the extension member 105 has a thin inner layer 325 around the flow channel 124 which is of a biocompatible fluid impermeable material such as a polymer (Teflon®) or a metal such as a stainless steel. A flexible vapor delivery extension member can include an electroless plating over a polymer base to provide biocompatible inner layer 325. Outward from the inner layer 325 is the insulating region or layer 320 that can comprise air channels, voids with a partial vacuum, a region that carries an aerogel or aerogel particles optionally under a partial vacuum, a region that carries hollow glass or ceramic microspheres, or a region with a channel or multiple channels that provide for a flow of air or a liquid about the at least one flow channel 124. An extension member 105 that includes flow channels or recirculation channels can be coupled to any positive and negative pressure sources known in the art to cause a flow of air, cooling fluids, cryogenic fluids and the like through such channels. The exterior 326 of the wall 324 can be any suitable layer of a high temperature resistant polymer such as PEEK. Other materials used in an extension member can comprise formulations or blends of polymers that include, but are not limited to PTFE, polyethylene terephthalate (PET), or PEBAX. PTFE (polytetrafluoroethylene) is a fluoropolymer which has high thermal stability (up to 260° C.), is chemically inert, has a very low dielectric constant, a very low surface friction and is inherently flame retardant. A range of homo and co-fluoropolymers are commercialized under such names as Teflon®, Tefzel®, Neoflon®, Polyflon® and Hyflon®. In one embodiment, the insulative layer 320, or inner layer 325 and insulating layer 320 in combination, or the entire wall 324, can have a thermal conductivity of less than 0.05 W/mK, less than 0.01 W/mK or less than 0.005 W/mK. In another aspect of the invention, the wall is configured at least partially with materials interfacing the channel that have a heat capacity of less than 2000 J/kgK for reducing condensation in the flow channel upon the initiation of vapor flow therethrough.

Figure 13A:
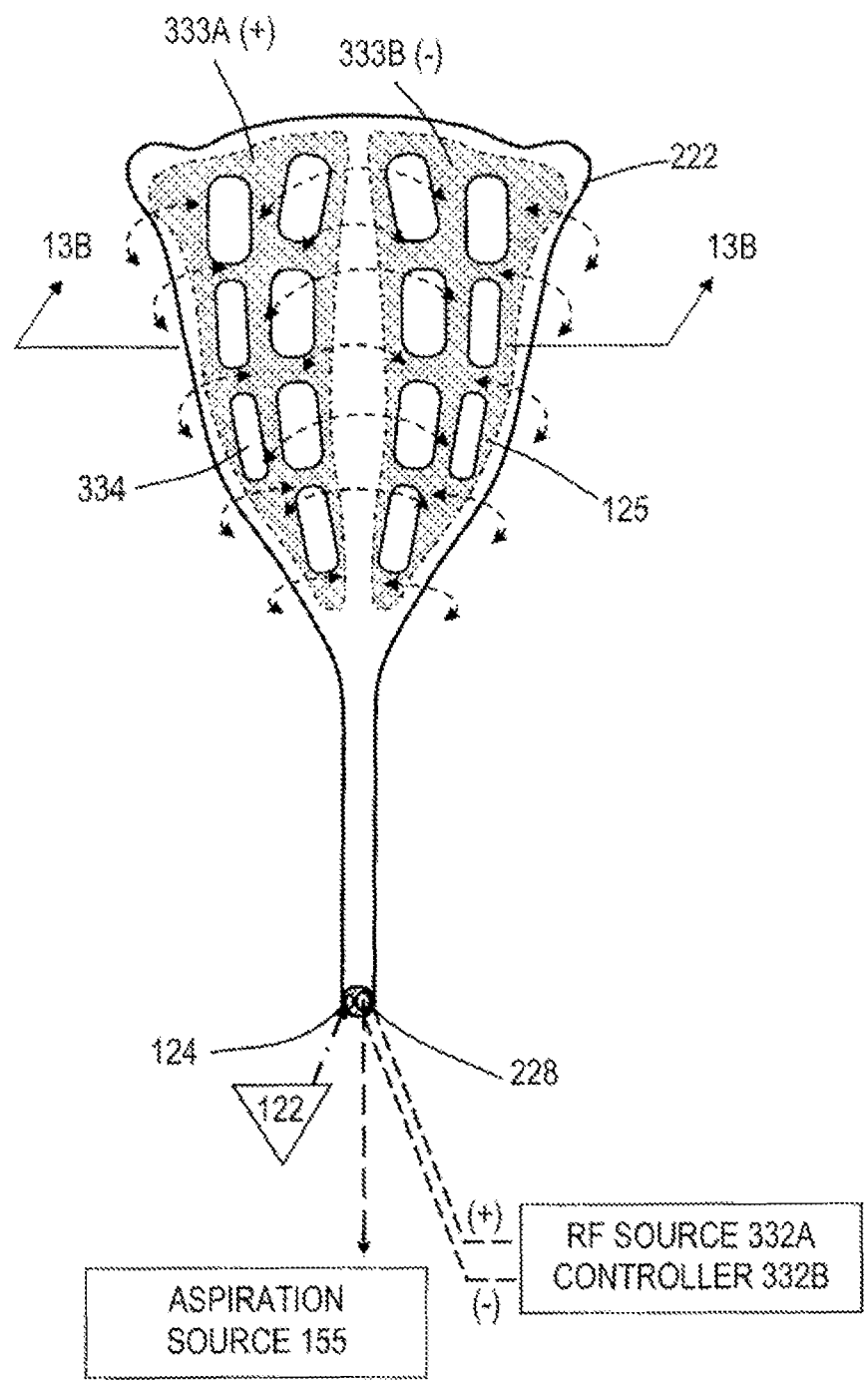
FIG. 13A is an illustration of another expandable working end with a surface electrode arrangement.
Figure 13B:
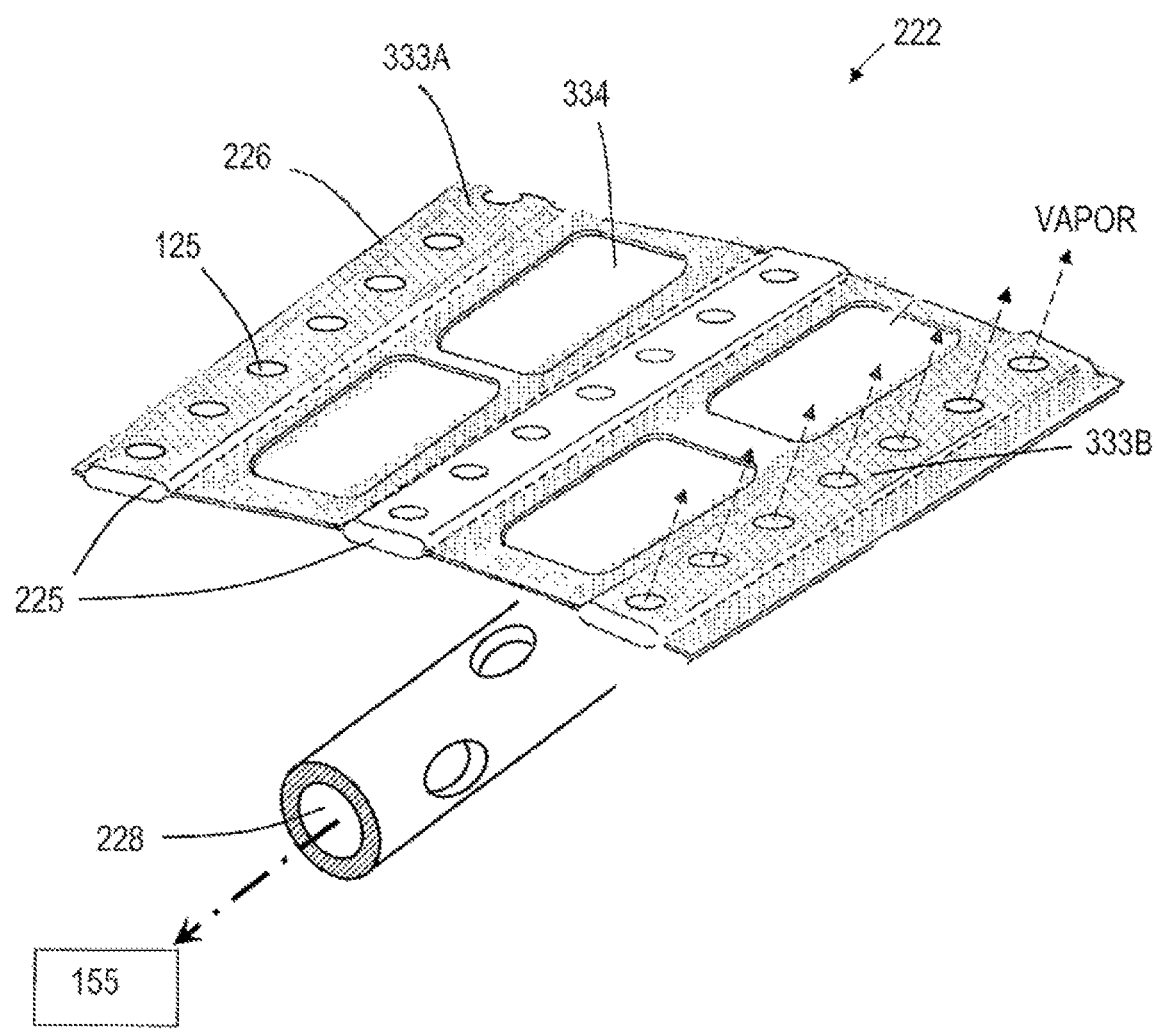
FIG. 13B is a sectional view of the expandable working end of FIG. 13A.

FIGS. 13A-13B illustrate another system with expandable working end similar to that of FIGS. 12A-12B with an additional energy delivery system carried by the expandable structure 222. As can be seen in FIG. 13A, the surface of expandable structure 222 carries at least one electrode arrangement operatively coupled to an electrical source such as an Rf source 332A and Rf controller 332B. The energy delivery system can comprise a surface electrode on the expandable structure 222 that cooperates with a ground pad, or as shown in the FIG. 13A, the system can carry spaces apart bi-polar electrodes that can comprise conductive coatings on a non-compliant balloon. In one embodiment of FIG. 13A, opposing polarity (+) and (−) electrodes 333A and 333B are shown and are adapted to apply energy to tissue as well as vapor 122 that exits the outlets 125. The current flows between the electrodes 333A and 333B are indicated by dashed lines in FIG. 13A, with such electrodes spaced apart is four quadrants around the structure. It should be appreciated that such spaced apart bi-polar electrode pairs can number from 2 to 100 or more about the surface of the structure. In one embodiment, hypertonic saline is vaporized to provide the flow of vapor 122 and saline droplets which will enhance Rf energy delivery to the tissue. FIG. 13B shows a cross section of a portion of wall 226 of the expandable structure of FIG. 13A wherein the interior chambers 225 (collectively) are channels in a thin film structure wall with outlets indicated at 125. In one embodiment, as in FIGS. 13A and 13B, the larger openings 334 permit vapor in the cavity extracted by a central aspiration or recirculation channel 228 at the interior of the structure similar to that of FIG. 11. The illustration of FIG. 13B does not show the interior constraining elements 242 as in FIG. 12B, but it should be understood that any number of such elements are possible to provide an asymmetric-shaped structure when pressurized.

In a method of use in treating the interior of an organ, with reference to FIGS. 12A, 12B and 12C, one method includes introducing the working end of an elongated probe introduction into a uterine cavity, providing a flow of a vapor media derived from water or saline from at least one outlet 125 in the working end 110 wherein the flow media applies a selected level of thermal energy to ablate at least portions of the endometrium. As described above, the ablation method is accomplished by allowing the vapor to collapse or condense to thereby release the heat of vaporization to uniformly ablate surface layers of the endometrium. Stated another way, the method includes converting the flow media from a first phase to a second phase thereby controllably applying thermal energy to the endometrium. One method includes introducing the flow media at a flow rate of ranging from 0.001 to 20 ml/min, 0.010 to 10 ml/min, 0.050 to 5 ml/min. One method includes introducing the flow media at an inflow pressure ranging from 0.5 to 1000 psi, 5 to 500 psi, and 25 to 200 psi. One method further includes applying the selected level of thermal energy over an interval ranging from 0.1 to 600 seconds; 0.5 to 300 seconds, and 1 to 180 seconds. Another method as described above includes providing a flow of a second media for combining with the vapor 122 to alter the average mass temperature of the combined vapor and second media.

In another aspect of the method of treating a uterus or the interior of another hollow organ, with reference to FIG. 12C, the system can be used to control the pressure within the uterus or other organ with controller 150 as described above. In one method, the controller 150 can control pressure in the cavity by modulating the inflow pressure of the flow media 122. In a related method, the controller 150 can control pressure by providing an outflow passageway in the probe for reducing pressure in the cavity. In an endometrial ablation procedure, the method includes providing a pressure in the uterus ranging between 0.1 psi and 6 psi, between 0.2 psi and 4 psi, and between 0.5 psi and 2 psi. This method includes controlling pressure in the uterus to distend the uterus during treatment. These methods also can be used when distending the uterus with an expandable working end.

Recirculation Channel, Flow Control, Insulative Subsystems

Figure 14A:
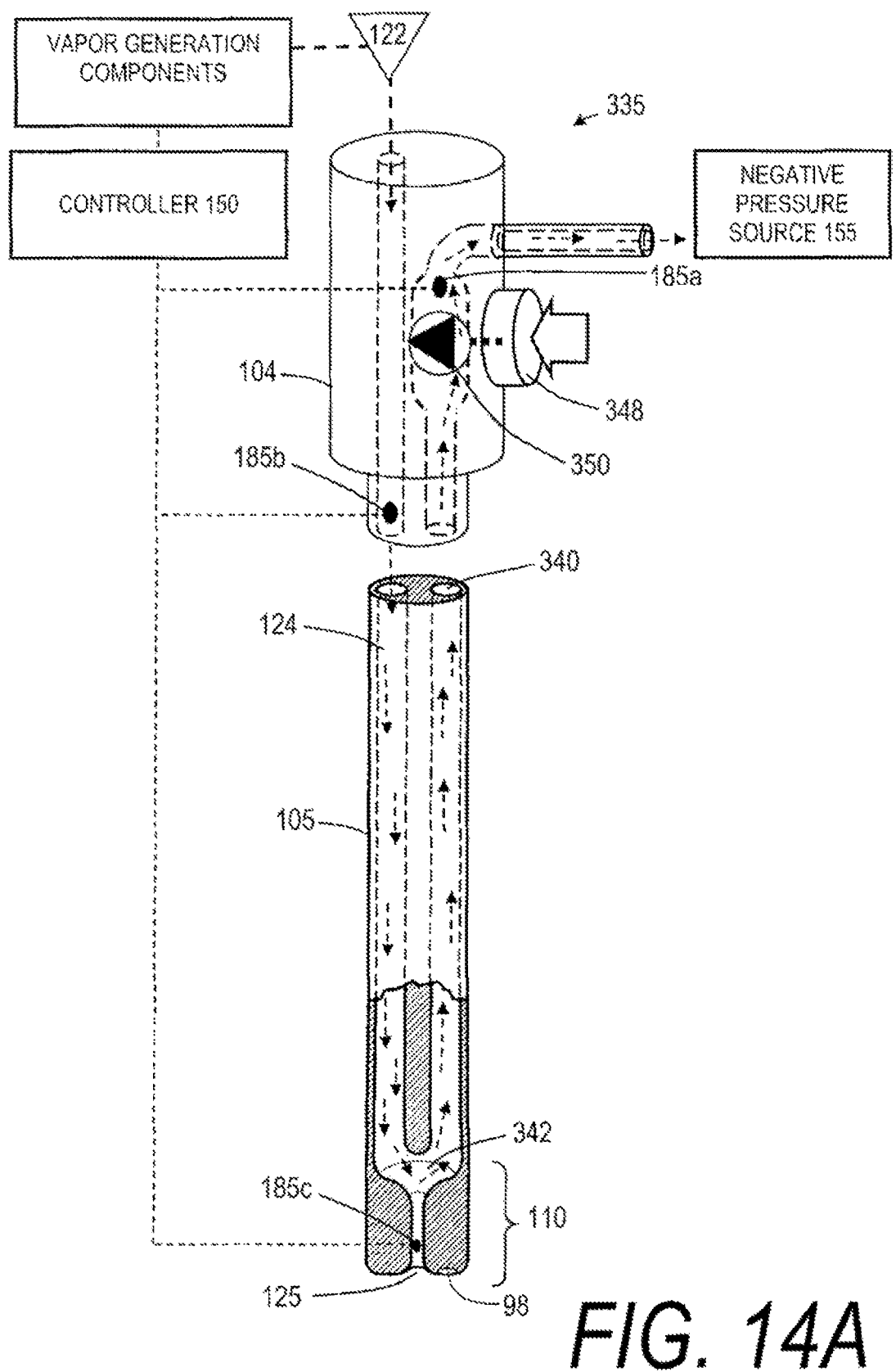
FIG. 14A is an illustration of a working end with a recirculation channel and valve for controlling vapor flows from the working end.
Figure 14B:
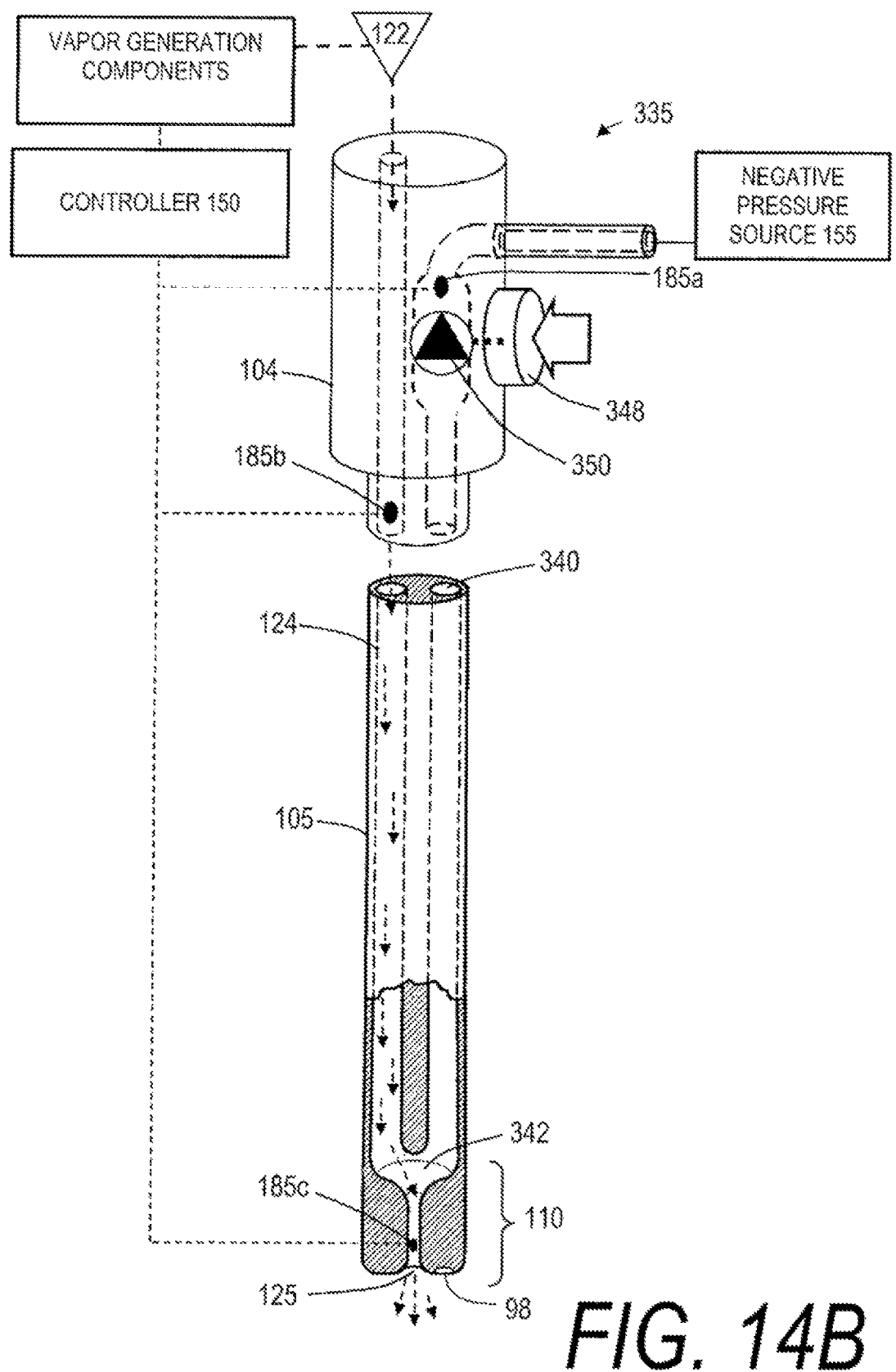
FIG. 14B is another view of the working end of FIG. 14A with the recirculation channel and valve in a different configuration.

FIGS. 14A and 14B depict another vapor deliver probe 335 with extension member 105 that can include the sensor subsystems as in the probe of FIG. 7 and additionally is configured with a second or recirculating flow channel 340 in the probe and extension member 105 that extends back to vent recirculation flows and optionally communicates with a negative pressure source 155 as depicted in FIG. 2. In one embodiment, the second channel or recirculating channel 340 is configured for controlling vapor flows to the outlet 125, which for example can be a single outlet or a plurality of outlets as in any embodiment described previously. In FIG. 14A, it can be seen that vapor media 122 generated by vapor generating components as described above and controller 150 to provide a pressurized vapor flow that flows distally through channel 124 and then reverses direction to flow in the proximally direction within channel region 342 that transitions into the second or recirculating channel 340. It can be understood that vapor media flows will continue in path of channel 124 and recirculation channel 340 so long as flow resistance is less through this pathway than through the small cross-section vapor outlet 125. In this aspect of the invention, the collective cross-section of the outlet(s) 125 is substantially less than the cross-section of the recirculating channel 340, for example, less than 20% of the recirculating channel 340, less than 10% of the recirculating channel 340, or less than 5% of the recirculating channel 340. The system includes means for closing the recirculating channel 340 to thus force vapor media 122 through the at least one outlet 125 to provides a "passive valve" at the outlet 125 and a method of instantly turning on a vapor flow from outlet 125 when operating a vapor generator in a continuous mode. In FIGS. 14A and 14B, it can be seen that a manual switch 348 in the handle portion 104 can operate valve 350 to block the recirculating channel 340 thus providing the passive valve that comprises the reduced cross-section outlet 125 at the working end. This form of passive valve is very useful in small diameter elongated extension members 105 such as an elongate flexible catheter. The switch can be in a proximal handle end 102 of the probe or optionally in a negative pressure source 155 coupled to recirculating channel 340 and can be operated by controller 150. In FIG. 14A, it can be understood that negative pressure source 155 can be operated to assist in exhausting vapor media from the recirculating channel 340 to enhance the recirculating flows. While the embodiment of FIGS. 14A-14B illustrates parallel channels 124 and 340, the channels can be varied, for example being concentric as described further below, or varied in cross section and/or length. The embodiment of FIGS. 14A-14B depict a blunt-tip working end 110 that can be used when injecting vapor into a lumen or body cavity such as a patient's respiratory tract, blood vessel, uterus, gastrointestinal tract and the like. It can be understood that a sharp-tip needle can be coupled to the distal end of the extension member 105 of FIGS. 14A-14B so that the passive valve is close to a needle that is configured to penetrate tissue for interstitial vapor delivery.

The embodiment of FIGS. 14A and 14B further illustrates a sensor system with temperature sensors 185a-185c as described above in the embodiment of FIG. 7. In addition, FIGS. 14A and 14B illustrate a visualization element 98 placed within a probe 335. In this variation the visualization element 98 is located in a working end 110 of the probe 335. However, the visualization element 98 can be located in any region of the device either by being placed within the device or otherwise attached to the device. Any number of visualization element 98 can be incorporated with the methods and devices described herein. For example, a visualization element 98 can include an optic fiber advanced within or adjacent to the device, a CCD camera affixed to the device or other visualization means as commonly used in remote visualization applications. The visualization element 98 can provide imaging before, during, and/or after the controlled flow egresses from the device. In addition, the visualization element can include thermal imaging capabilities to monitor the vapor flow from the device or the treatment effect in tissue.

In another aspect of the invention, the method of controllably applying energy to tissue utilizing the system and methods described above provides for the ablation and complete resorption or substantially complete resorption of ablated tissue, which is termed herein "resorptive ablation" of tissue. In general, the term "tissue resorption" is used herein to describe the process in which a differentiated body structure undergoes lysis and assimilation into the body. Alternatively stated, the biological process of resorption comprises the destruction, disappearance, and/or dissolution of a tissue or a body structure by natural biochemical activity of the body. The ablation of tissue comprises cell death in the treated tissue.

In most, if not all, ablative treatments of tissue, it would be preferable to have treated tissue be entirely resorbed and disappear (sec treated tissue of FIGS. 4A-4B and FIGS. 9A-11). For example, in a tumor ablation treatment or in the treatment of benign tissue such as a fibroid, it would be preferred if all targeted tissue and body structure disappeared following treatment and the passage of time needed for tissue resorption. In the treatment of prostatic tissue to achieve intracapsular volume reduction, it would be preferred if all ablated tissue would be resorbed. In the ablative treatment of lung tissue to reduce lung volume, it would be preferred if an ablated bronchial segment would be entirely resorbed. In the treatment of varicose veins, it would be preferred if all ablated vessel segments would be resorbed. In sealing or coagulating tissues, it also would be preferred if the coagulated tissue would be resorbed.

It is known that conventional electrosurgical devices, laser devices and HIFU devices can generate high peak temperatures in local regions of a tissue volume targeted for ablation. Such high, local peak temperatures, which result from lack of control over energy densities in the tissue, can cause "fixation" of tissues similar to the manner in which chemical fixatives cause tissue fixation. Conventional chemical fixation of tissue involves the chemical alteration of proteins to prevent breakdown, and in many cases such chemical cross-linking fixatives act by creating covalent chemical bonds between soluble proteins and the cytoskeleton which preserves tissue as well as adding rigidity to the tissue. For example, dilute formalin solutions are known as effective fixatives for tissue preservation.

Another type of fixation known in the art of tissue preservation is called heat fixation or thermal fixation. Heat fixation creates new cross-linking bonds between proteins, and is typically used to preserve thin tissue sections on slides. In-vivo tissue treatments have noted cell death by such "heat fixation" in a treatment of breast cancer. For example, high-intensity-focused ultrasound (HIFU) was investigated as a noninvasive thermal ablation technique. "Heat fixation of cancer cells ablated with high-intensity focused ultrasound in patients with breast cancer". F. Wu, et al., *The American Journal of Surgery*. Volume 192, Issue 2, Pages 179-184.

Thus, high peak temperatures in prior art ablative treatments can cause the equivalent of heat fixation of tissues—which in turn can prevent tissue resorption. For this reason, electrosurgical, light energy and HIFU modes of tissue ablation may in all cases cause localized tissue fixation within or throughout regions of ablation thus preventing complete tissue resorption.

In general, a method of the invention comprises ablating a targeted tissue volume with a controlled form of energy delivery that allows for complete resorption of ablated tissue. It has been found that if (i) energy delivery is entirely uniform within a targeting tissue volume within an ablative time-temperature range, and (ii) energy delivery causes no portion of the targeted tissue volume to reach a "heat fixation" temperature, then the ablative tissue can be entirely resorbed by the body.

In one aspect of the invention, a method of applying energy to tissue by means of energy released from the phase change of vapor media has been found to be effective in providing uniform thermal effects in tissue and further insuring that no tissue is elevated in temperature above the heat fixation range. Additional examples of systems, devices, and methods of energy delivery can be found in the patent applications and patents referenced herein.

Figure 15A:
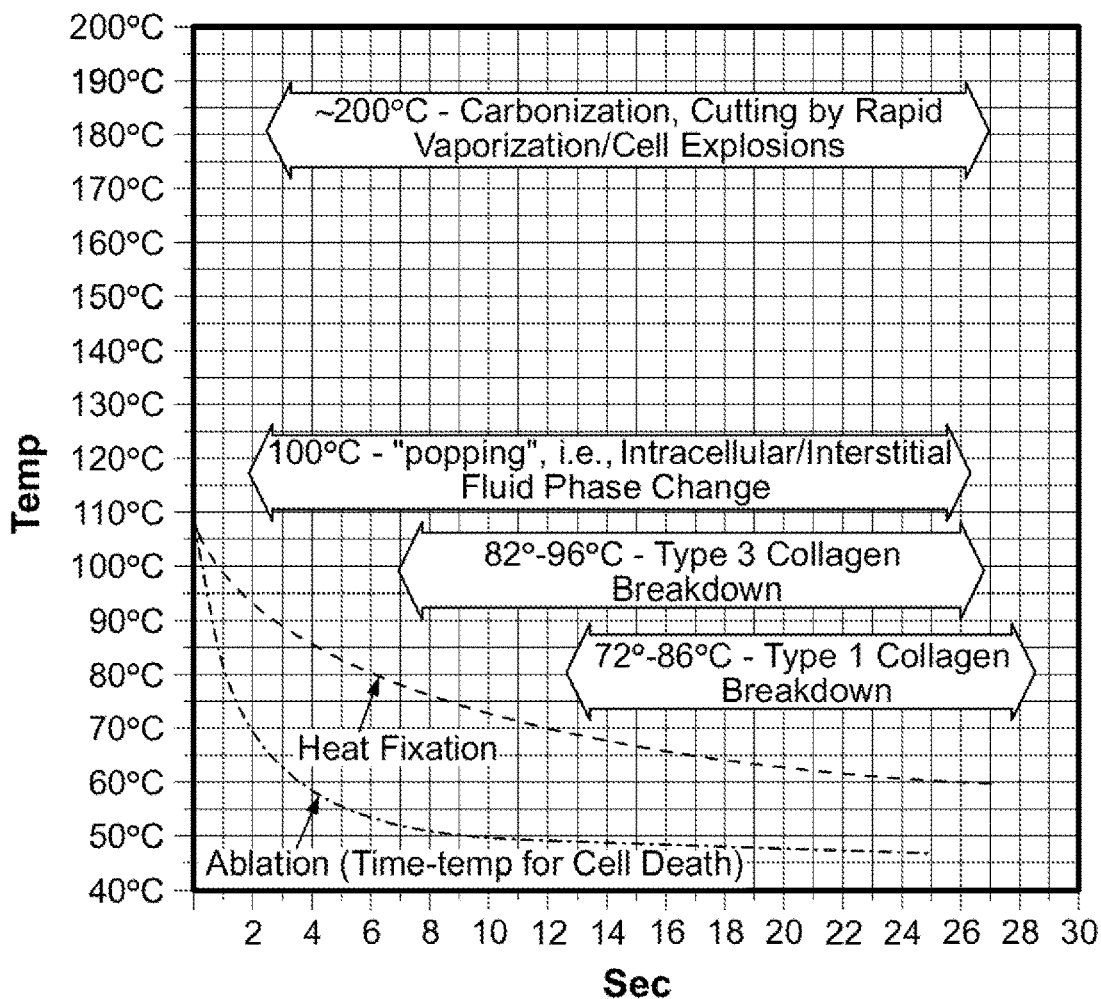
FIG. 15A illustrates a time-temperature curve that indicates cell death as well as a curve which indicates time-temperature parameters that can cause heat fixation of tissues.

Following testing in animal models, it has been found that certain time-temperature parameters are required to "ablate" tissue, which term is used herein to describe cell death in the targeted tissue volume. FIG. 15A illustrates a time-temperature curve that indicates such cell death. The chart of FIG. 15A further includes a curve which indicates time-temperature parameters that can cause heat fixation of tissues.

In the upper portion of chart of FIG. 15A, ranges of temperature are illustrated that cause certain thermal effects in tissue, which effects can be a factor in the heat fixation of tissue. For example, at temperatures of about 72° C. to 86° C., Type 1 collagen is denatured. At temperatures of about 82° C. to 96° C., Type 3 collagen is denatured. Also, at temperatures of about 64° C. to 78° C., Type 2 collagen breaks down (not shown). Also shown in the chart of FIG. 15A, an effect that is very common in RF energy delivery to tissue is commonly called "popping" which occurs when tissue temperature reaches 100° C. and intracellular and interstitial fluid undergoes a phase change and makes a popping sound. Also shown in FIG. 15A, at about 200° C., the tissue can undergo such rapid vaporization and/or cell explosions that tissue cutting will be the result, as well as tissue carbonization. All of these thermal effects in tissue can locally or regionally cause a transformation in tissue causing heat fixation of tissue. Once transformed, heat fixated tissue prevents or impedes the complete, rapid resorption of the ablated tissue.

Figure 15B:
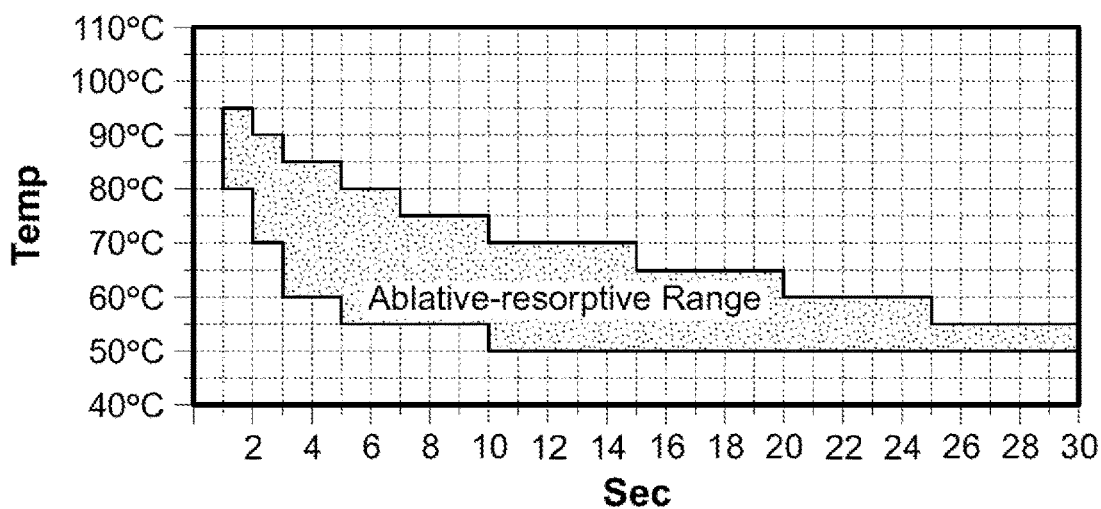
FIG. 15B illustrates an envelope of treatment parameters that allow for ablation and resorption ("ablative-resorptive" range) which correlates to the chart of FIG. 15A.

A method of the invention thus comprises an ablative-resorptive tissue treatment method, wherein the energy delivery and resulting thermal effects are sufficient to cause cell death (see ablation time-temp curve of chart of FIG. 15A) but do not exceed the time-temperature parameters that could cause transformation of the treated tissue such that the tissue undergoes heat fixation (see the heat fixation curve of FIG. 15A). In general, the claimed method and envelope of treatment parameters that allow for ablation and resorption ("ablative-resorptive" range) is illustrated in the chart of FIG. 15B. Initial studies indicate that tissue temperature in the 90°-95° C. range for greater than about 1 second can begin to cause heat fixation. In lower tissue ranges, tissue temperatures in the 50°-55° C. range for greater than about 30 seconds can cause heat fixation. Other intermediate time-temperature ranges are shown that provide effective ablation and allow for resorption.

Thus, a method of the invention comprises selecting a tissue volume or body structure targeted for ablation and resorption, controllably applying energy to the selected tissue volume in the ablative-resorptive range of the chart shown in FIG. 15B, and utilizing a mode of energy delivery that prevents any focused energy densities within the selected tissue volume. The selected tissue can be a three-dimensional block of tissue or wall portion of a body orifice, passageway, opening, cavity, lumen, vessel or sinus—all of which can be ablated uniformly using the apparatus and methods described above. The tissue can comprise portions of a body structure including an eye, brain, sinus, nasal passageway, oral cavity, blood vessel, arteriovascular malformation, heart, airway, lung, bronchus, bronchiole, larynx, trachea, Eustachian tube, uterus, vaginal canal, esophagus, stomach, duodenum, ileum, colon, rectum, bladder, urethra, ureter, vas deferens, prostate, kidney, gall bladder, pancreas, bone, joint capsule, tumor, fibroid, benign tissue mass, vascularized tissue mass, hemorrhoid, tissue mass including a plexus of dilated veins, a neoplastic mass and a cyst.

As noted in FIG. 15A, controlling the temperature of the tissue to cause ablation but prevent transformation of the tissue that will result in heat fixation can be performed a number of ways. For example, since the transformation limit of the tissue is dependent upon the treatment duration or activation time, preventing transformation of the tissue can occur by limiting the time of treatment. In another variation, controlling the temperature of the tissue can be achieved by controlling a temperature of the vapor media. In such a case, as described in the applications referenced above, a particular flow media can be selected, which upon conversion to the vapor media, limits temperature in the vapor media or limits the amount of energy delivered to the tissue. For example, the systems and methods described herein can vaporize alcohol which will lower the amount of energy delivered per unit volume of vapor as well as enhance the thermal ablation.

In an additional variation, a separate media can be combined with the vapor media to control temperature of the tissue. In one example, this separate media can be combined with the vapor media where the separate media comprises a lower or higher heat of vaporization than the flow media. This combination can control the temperature of the heat of vaporization which in turn controls the release of energy for ablating tissue. Such system systems described herein (as well as those described in the patents and applications incorporated by reference) can include a secondary pressurized media inflow source that is adapted to introduce media or a substance (in the form of at least one of a gas, liquid or particulate) through the device for combining with vapor media after it is ejected from the device to the tissue. The addition of the separate media allows for controlling the average mass temperature of the vapor that is delivered to the tissue. The separate media includes, but is not limited a bioinert gas or atomized fluid that is depressurized and introduced into the vapor for the purpose of reducing the mass average temperature of the injected media to lower than about 100° C. For example, the introduced media 310 can be depressurized $CO_2$, $N_2$, or $O_2$ or atomized $H_2O$. By this means, the mass average temperature can be less than 100° C., for example in the range of about 45° C. to 100° C.

In another variation, the systems and methods described herein can introduce additional therapeutic media that comprises a pharmacologically active substance with the vapor stream, such as any suitable anesthetic, to interact with tissue. In a similar embodiment and method of the invention, the systems described above can introduce additional media or substance that enhances ablation or damage of the targeted tissue such as any sclerosing agent. The substance also can be ethyl alcohol that enhances damage to the tissue targeted for treatment. Another example of the therapeutic media includes any toxin, e.g., Botulinum Toxin Type A, that can enhance local tissue damage. Another variation of a therapeutic media includes Tetracyline or any another antibiotic substance that damages tissues to promote a more robust immune response for ablation procedures in which greater collagen formation of adhesions are preferred.

In one aspect of the invention the applied energy is provided by condensation of a vapor media, with the targeted tissue volume comprising the lining of a body cavity or lumen. In another aspect of the invention, the targeted tissue volume comprises a tumor, neoplastic tissue or hypertrophic tissue.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of applying energy to a region of tissue using an energy delivery device to cause resorption of the region of tissue by a body, the method comprising:
   applying an energy from the energy delivery device to the region of tissue for an activation time where the energy is uniformly delivered to prevent regions of high energy density in the region of tissue; and
   ablating the region of tissue using a controller coupled to the energy delivery device configured to control the energy such that the controller maintains a temperature of the region of tissue over the activation time to remain between a first target temperature that causes ablation over the activation time and a second temperature, which prevents heat fixation of the region of tissue to allow resorption of the region of tissue where the second temperature is below a temperature that denatures collagen in the tissue over the activation time.

2. The method of claim 1, where resorption of the region of tissue comprises destruction, disappearance, and dissolution of the region of tissue by a natural biochemical activity of the body.

3. The method of claim 1, where the second target temperature is dependent upon the activation time.

4. The method of claim 1, where applying energy comprises delivering a vapor media to the region of tissue where upon contacting the region of tissue energy transfer occurs between the vapor media and the region of tissue.

5. The method of claim 4, where controlling the energy such that the region of tissue remains below the second temperature comprises controlling a temperature of the vapor media.

6. The method of claim 5, where controlling the temperature of the vapor media comprises combining the vapor media with a second media to control the temperature.

7. The method of claim 4, further comprising introducing an additional therapeutic media with the vapor media.

8. The method of claim 7, where the additional therapeutic media enhances ablation of the region of tissue.

9. The method of claim 1, where applying energy to the region of tissue comprises inserting an energy delivery device into the body to the region of tissue.

10. The method of claim 9, where the region of tissue is selected from a group consisting of a tissue structure, a wall of tissue, a body orifice, a passageway in the body, a cavity within the body, a lumen in an organ, and a vessel.

11. The method of claim 9, where the region of tissue comprises a region selected from a group consisting of: an eye, brain, sinus, nasal passageway, oral cavity, blood vessel, arteriovascular malformation, heart, airway, lung, bronchus, bronchiole, larynx, trachea, Eustachian tube, uterus, vaginal canal, esophagus, stomach, duodenum, ileum, colon, rectum, bladder, urethra, ureter, vas deferens, prostate, kidney, gall bladder, pancreas, bone, joint capsule, tumor, fibroid, benign tissue mass, vascularized tissue mass, hemorrhoid, tissue mass including a plexus of dilated veins, a neoplastic mass and a cyst.

12. The method of claim 9, further comprising moving the energy delivery device while applying the energy.

13. The method of claim 1, where the region of tissue comprises a tissue selected from a group consisting of a neoplastic tissue, a hypertrophic and hyperplastic tissue.

14. A method of ablating a region of tissue using an energy delivery device coupled to a controller, the method comprising:
   providing an energy supply from the controller that delivers energy to the energy delivery device to apply energy in a uniform manner to the region of tissue such that the energy does not contain any regions of high energy density; and
   controlling the energy supply to deliver energy to the region of tissue to alter a treatment temperature of the region of tissue for an activation time such that the controller maintains the treatment temperature of the region of tissue above a first target temperature that causes ablation of the region of tissue over the activation time and below a second target temperature that causes a fixation transformation of the region of tissue where the second target temperature is also below a temperature that denatures collagen in the tissue over the activation time, and
   where the fixation transformation would otherwise prevent resorption of at least a portion of the region of tissue.

15. The method of claim 14, where resorption of the region of tissue comprises destruction, disappearance, and or dissolution of the region of tissue by a natural biochemical process of a body.

16. The method of claim 14, wherein controlling the energy supply to deliver energy comprises delivering a vapor media to the region of tissue where upon contact with the region of tissue energy transfer occurs between the vapor media and the region of tissue.

17. The method of claim 16, where controlling the energy supply comprises controlling a temperature of the vapor media.

18. The method of claim 17, where controlling the temperature of the vapor media comprises combining a second media with the vapor media to control the temperature.

19. A method of applying energy to a region of tissue using an energy delivery device coupled to a controller to cause resorption of the region of tissue by a body, the method comprising:
    producing a vapor media by applying an amount of energy to a fluid media in the energy delivery device;
    directing the vapor media from the energy delivery device to the region of tissue for a treatment time, where the vapor media delivers energy uniformly within the region of tissue such that a temperature of the region of tissue rises above an ablation temperature, where the ablation temperature is dependent upon the treatment time;
    controlling the amount of energy applied to the fluid media using the controller such that the temperature of the region of tissue is sufficient to ablate the region of tissue; and
    altering the temperature depending on the treatment time such that the controller maintains a temperature of the region of tissue between a first target temperature that causes ablation over the treatment time and below a second temperature, where maintaining the temperature of the region prevents heat fixation of tissue that would otherwise prevent resorption of at least some of the region of tissue, and
    where the second temperature is also below a temperature that denatures collagen in the tissue over the treatment time.

20. The method of claim 19, where resorption of the region of tissue comprises destruction, disappearance, and or dissolution of the region of tissue by a natural biochemical activity of the body.

21. The method of claim 19, where controlling the amount of energy applied to the fluid media such that the region of tissue remains below the second temperature comprises controlling the amount of energy applied to the fluid media such that the region of tissue remains below a heat fixation temperature, where the heat fixation temperature is dependent upon the activation time of the energy.

22. The method of claim 19, where controlling the amount of energy applied to the fluid media such that the region of tissue remains below the second temperature comprises controlling a temperature of the vapor media.

23. The method of claim 22, where controlling the temperature of the vapor media comprises combining the vapor media with a second media to control the temperature.

* * * * *